United States Patent
Ross et al.

(10) Patent No.: US 11,015,137 B2
(45) Date of Patent: May 25, 2021

(54) COMPOSITION, METHOD AND USE

(71) Applicant: Innospec Limited, Ellesmere Port (GB)

(72) Inventors: Alan Norman Ross, Wigan (GB); Martin Roberts, Tarleton (GB)

(73) Assignee: Innospec Limited, Ellesmere Port (GB)

( * ) Notice: Subject to any disclaimer, the term of this patent is extended or adjusted under 35 U.S.C. 154(b) by 0 days.

(21) Appl. No.: 16/494,959

(22) PCT Filed: Mar. 28, 2018

(86) PCT No.: PCT/GB2018/050847
§ 371 (c)(1),
(2) Date: Sep. 17, 2019

(87) PCT Pub. No.: WO2018/178693
PCT Pub. Date: Oct. 4, 2018

(65) Prior Publication Data
US 2020/0040270 A1 Feb. 6, 2020

(30) Foreign Application Priority Data
Mar. 30, 2017 (GB) .................................. 1705124

(51) Int. Cl.
| | |
|---|---|
| *C10L 1/222* | (2006.01) |
| *C07C 243/40* | (2006.01) |
| *C07C 235/74* | (2006.01) |
| *C07C 241/02* | (2006.01) |
| *C07C 219/06* | (2006.01) |
| *C07C 213/02* | (2006.01) |
| *C10L 1/06* | (2006.01) |
| *C10L 10/04* | (2006.01) |
| *C10L 10/08* | (2006.01) |
| *C10L 1/224* | (2006.01) |
| *C10M 133/06* | (2006.01) |

(52) U.S. Cl.
CPC .......... *C10L 1/2222* (2013.01); *C07C 213/02* (2013.01); *C07C 219/06* (2013.01); *C07C 235/74* (2013.01); *C07C 241/02* (2013.01); *C07C 243/40* (2013.01); *C10L 1/06* (2013.01); *C10L 1/224* (2013.01); *C10L 10/04* (2013.01); *C10L 10/08* (2013.01); *C10M 133/06* (2013.01); *C10L 2200/0423* (2013.01); *C10L 2230/22* (2013.01); *C10L 2270/023* (2013.01); *C10M 2215/26* (2013.01)

(58) Field of Classification Search
CPC combination set(s) only.
See application file for complete search history.

(56) References Cited

U.S. PATENT DOCUMENTS

| | | | |
|---|---|---|---|
| 2,812,342 A | 11/1957 | Peters | |
| 3,110,673 A | 11/1963 | Benoit, Jr. | |
| 3,172,892 A | 3/1965 | Le Suer | |
| 3,216,936 A | 11/1965 | Le Suer | |
| 3,219,666 A | 11/1965 | Norman | |
| 3,250,715 A | 5/1966 | Wyman | |
| 3,251,853 A | 5/1966 | Hoke | |
| 3,260,671 A | 7/1966 | Trites | |
| 3,272,746 A | 9/1966 | Le Suer | |
| 3,275,554 A | 9/1966 | Wagenaar | |
| 3,310,492 A | 3/1967 | Benoit, Jr. | |
| 3,326,801 A | 6/1967 | Schlobohm | |
| 3,337,459 A | 8/1967 | Ford | |
| 3,341,542 A | 9/1967 | Le Suer | |
| 3,405,064 A | 10/1968 | Miller | |
| 3,429,674 A | 2/1969 | Hoke | |

(Continued)

FOREIGN PATENT DOCUMENTS

| | | |
|---|---|---|
| CA | 1109753 | 9/1981 |
| CN | 1109753 A | 9/1981 |

(Continued)

OTHER PUBLICATIONS

International Search Report and Written Opinion issued in PCT/GB2018/050847 dated Jun. 11, 2018.
Combined Search and Examination Report issued in Application No. GB1805095.5 dated Nov. 16, 2018.
Search Report issued in Application No. GB1705124.4 dated Jan. 22, 2018.
W. Qioa et al., "Synthesis and Characterization of a Novel Series of Cationic Fumaric Polymerizable Emulsifiers" Journal of Surfactants and Detergents, vol. 14, No. 1, pp. 37-41, 2011.
I. Bityukova et al., "Analogs of Acetylcholine an Diacetylcholine Containing Aamantyl Radicals", p. 543, 1982.
D. A. Jaeger et al., "Regioselectivity Control in Diels-Alder Reactions of Surfactant 1,3-Dienes with Surfactant Dienophiles", Journal of the American Chemical Society, vol. 122, No. 12, pp. 2749-2757, 2000.

(Continued)

*Primary Examiner* — Ellen M McAvoy
*Assistant Examiner* — Chantel L Graham
(74) *Attorney, Agent, or Firm* — Burns & Levinson LLP; Janine M. Susan

(57) ABSTRACT

A quaternary ammonium salt of formula (I): wherein X is a linking group; Y is O, NH or $NR^1$ wherein $R^1$ is H or an optionally substituted hydrocarbyl group; $Q^+$ is a moiety that includes a quaternary ammonium cation; $A^-$ is an anion; $R^2$ is an optionally substituted alkylene group; $R^3$ is hydrogen or an optionally substituted hydrocarbyl group; and n is 0 or a positive integer; provided that n is not 0 when $R^3$ is hydrogen.

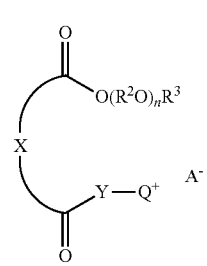

(I)

23 Claims, 1 Drawing Sheet

(56) References Cited

U.S. PATENT DOCUMENTS

| | | | |
|---|---|---|---|
| 3,438,757 | A | 4/1969 | Honnen |
| 3,444,170 | A | 5/1969 | Norman |
| 3,454,555 | A | 7/1969 | van der Voort |
| 3,455,831 | A | 7/1969 | Davis |
| 3,455,832 | A | 7/1969 | Davis |
| 3,468,639 | A | 9/1969 | Lindstrom |
| 3,565,804 | A | 2/1971 | Honnen |
| 3,576,743 | A | 4/1971 | Widmer |
| 3,630,904 | A | 12/1971 | Musser |
| 3,632,511 | A | 1/1972 | Liao |
| 3,755,433 | A | 8/1973 | Miller |
| 3,804,763 | A | 4/1974 | Meinhardt |
| 3,822,209 | A | 7/1974 | Knapp |
| 3,857,791 | A | 12/1974 | Marcellis et al. |
| 4,234,435 | A | 11/1980 | Meinhardt et al. |
| 4,564,372 | A | 1/1986 | Campbell |
| 5,021,169 | A | 6/1991 | Shin et al. |
| 6,821,307 | B2 | 11/2004 | Caprotti et al. |
| 7,112,230 | B2 | 9/2006 | Malfer et al. |
| 7,491,248 | B2 | 2/2009 | Colucci et al. |
| 2008/0052985 | A1 | 3/2008 | Stevenson et al. |
| 2008/0113890 | A1 | 5/2008 | Moreton et al. |
| 2011/0258917 | A1 | 10/2011 | Garcia Castro et al. |
| 2011/0315107 | A1 | 12/2011 | Grabarse et al. |
| 2012/0010112 | A1 | 1/2012 | Grabarse et al. |
| 2013/0031827 | A1 | 2/2013 | Reid et al. |
| 2014/0174390 | A1* | 6/2014 | Reid ............ C10L 10/04 123/1 A |
| 2015/0322372 | A1* | 11/2015 | Gao ............ C10M 105/36 508/409 |

FOREIGN PATENT DOCUMENTS

| | | |
|---|---|---|
| CN | 106512024 A | 3/2017 |
| WO | 2001042399 A1 | 6/2001 |
| WO | 2003078553 A2 | 9/2003 |
| WO | 2006135881 A2 | 12/2006 |
| WO | 2011095819 A1 | 8/2011 |
| WO | 2013017889 A1 | 2/2013 |
| WO | 2015011506 A1 | 1/2015 |
| WO | 2015011507 A1 | 1/2015 |
| WO | 2015183916 A1 | 12/2015 |
| WO | 2015184251 A1 | 12/2015 |
| WO | 2016016641 A1 | 2/2016 |
| WO | 2016099995 A1 | 6/2016 |
| WO | 2017017454 A1 | 2/2017 |

OTHER PUBLICATIONS

I. D. Konstantinova et al., Synthesis of Cationic Ether Lipids of Alkyl type with short-chain substituents at the 2-position of the Glycerol Backbone, Russian Chemical Bulletin, vol. 43, No. 10, pp. 1731-1735, 1994.

Abele et al., "Cationic and Zwitterionic Polymerizable Surfactants: Quaternary Ammonium Dialkyl Maleates. 1. Synthesis and Characterization", Langmuir, vol. 15, pp. 1033-1044, 1999.

* cited by examiner

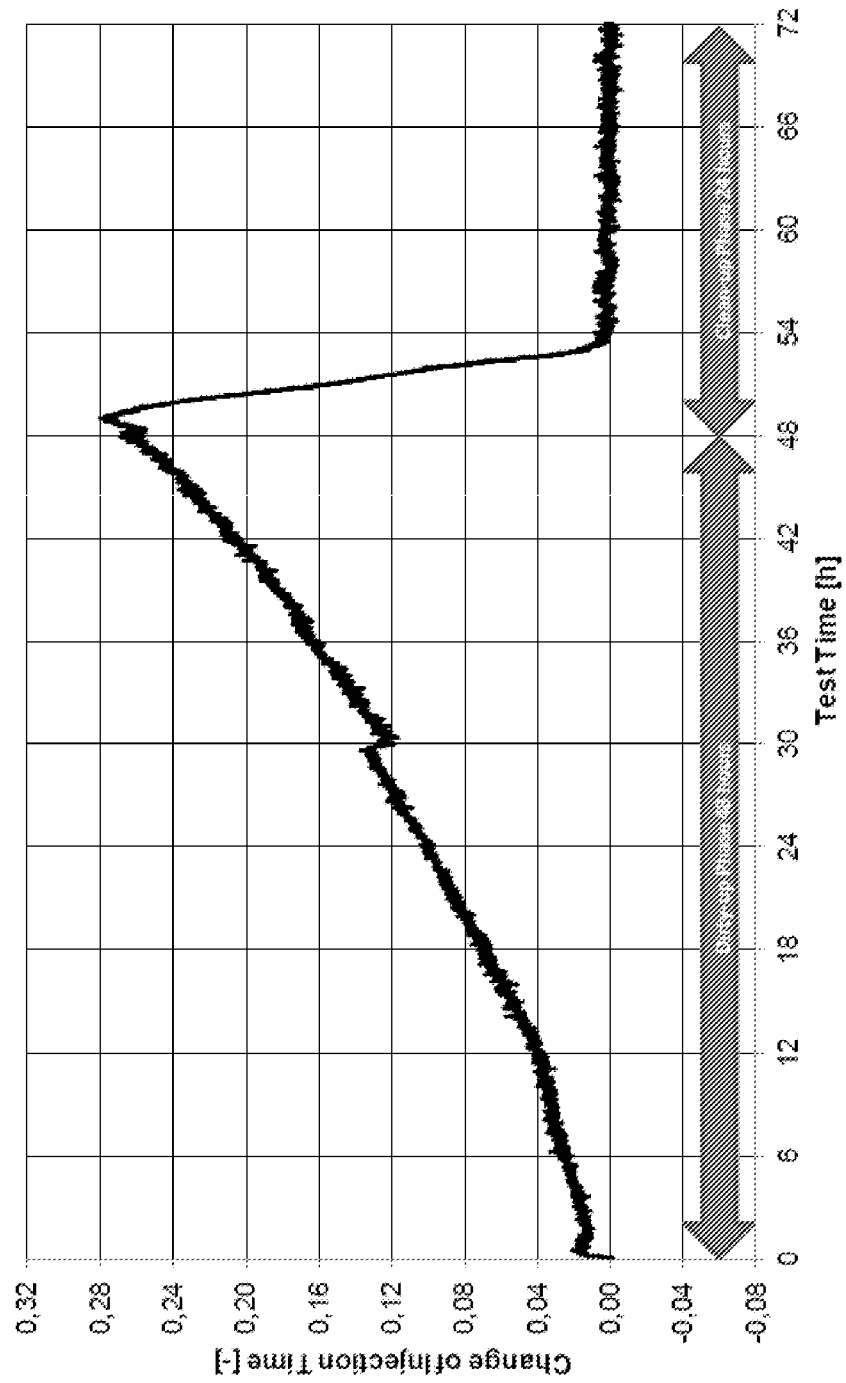

COMPOSITION, METHOD AND USE

CROSS-REFERENCE TO RELATED APPLICATIONS

This application is a U.S. national stage application under 35 U.S.C. 371 of co-pending International Application No. PCT/GB2018/050847, filed on Mar. 28, 2018, and entitled COMPOSITION, METHOD AND USE, which in turn claims priority to and benefit of Great Britain Patent Application No. 1705124.4, filed Mar. 30, 2017, which is incorporated by reference herein in its entirety for all purposes.

This present invention relates to fuel compositions, methods and uses relating thereto. In particular, the invention relates to ester additives for fuel used in spark ignition engines.

With over a hundred years of development the spark ignition (SI) engine has become a highly tuned piece of engineering. As the SI engine has become more highly tuned it has become more sensitive to variations in its construction. The construction of such engines can change with use as deposits build up on certain components and through wear of other components. These changes in construction may not only change parameters such as power output and overall efficiency; they can also significantly alter the pollutant emissions produced. To try and minimise these time-related changes to an engine's construction fuel additives have been developed to minimise wear and deposit build-up phenomena. Examples include anti valve seat recession additives to reduce wear and detergents to reduce deposit build-up.

As engine technology has evolved so have the demands put upon fuel additive packages. Early gasoline detergents were formulated to overcome the problem of deposit build-up on carburetors. In a carburetor a partial vacuum in part of the engine intake system is used to draw fuel into the induction system. To provide better control of the fuel air mixture carburetors were replaced with fuel injection equipment where a pressure above atmospheric pressure was used to force the fuel into the intake system and to induce better atomisation of the fuel.

As a replacement for carburetors so called throttle body injectors were used with just a single injector taking the place of the carburetor. The position of a throttle body injector was thus very similar to that of the carburetor and the temperature regime was thus similar.

To obtain greater control over the fuel delivery into the engine cylinders there was a move to using individual fuel injectors for each cylinder. These injectors were thus placed in the individual inlet ports for each cylinder; this configuration thus became known as port fuel injection or PFI. Because the fuel injector was now placed closer to the combustion chamber it tended to get hotter. Also as it was closer to the engine inlet port it was more likely to be subjected to exhaust gases passing back into the inlet system during the initial part of the inlet valve opening event. This made the injector more prone to deposit build up and thus increased the demands on the fuel additive required to minimise this deposit build-up.

The systems so far outlined were designed to provide an air fuel mixture that was approximately stoichiometric. The engine power was determined by the amount of stoichiometric mixture provided to the cylinder. This was controlled by restricting the flow of mixture into the cylinders, known as throttling. This inevitably incurred pumping losses thus reducing the efficiency of the overall system.

To overcome this problem engine designers have developed injection systems where the fuel is injected directly into the cylinder. Such engines are alternatively known as direct injection spark ignition (DISI), direct injection gasoline (DIG), gasoline direct injection (GDI) etc. Injecting directly into the combustion chamber allows for some degree of stratification of the charge thus allowing an overall lean mixture whilst having a local rich or stoichiometric mixture to facilitate reliable combustion. This injection strategy however means that the fuel injector is subjected to higher temperatures and pressures. This increases the likelihood of forming deposits from the high temperature degradation of the fuel. The fact that the injector is in the combustion chamber also exposes the injector to combustion gases which may contain partially oxidised fuel and or soot particles which may accumulate, increasing the level of deposits. The ability to provide good atomisation of fuel and precise control of fuel flow rates and injection duration are critical to the optimum performance of these engine designs. The radically different operating environment of the fuel injector poses a whole new set of design constraints on the development of an effective fuel additive package. Mixture stratification can also result in combustion occurring in local rich regions leading to the formation of soot particles which can increase combustion chamber deposits. Because liquid fuel is injected into the combustion chamber there is a greater risk of liquid impingement on the combustion chamber surfaces, particularly the piston crown. Liquid fuel on the combustion chamber surfaces can undergo thermal decomposition leading to gum formation and thus increase the rate of build-up of combustion chamber deposits.

An additional problem arising from injecting the fuel directly into the combustion chamber is that fuel impingement on the inlet valves is significantly reduced. The use of fuel containing detergents was relied upon to remove the deposits that build up on the inlet valve tulip as a result of lubricating oil passing down the valve stem and from combustion gases passing back into the inlet system during the initial part of the inlet valve opening event. In a direct injection engine the only possibility for fuel to impinge on the inlet valve tulip is from early injection and late inlet valve closing. This therefore makes it extremely difficult for a fuel borne detergent to have a significant effect on inlet valve deposits.

Effective control of deposits in a direct injection spark ignition gasoline engine is, therefore, a challenging task. Knowledge gained in using additives in other contexts, for example in gasoline engines using carburetors or in gasoline engines using an individual, common, fuel injector, or fuel injectors in the inlet port of each cylinder, or in diesel engines, appear to be of little assistance in achieving effective control of deposits in a direct injection spark ignition gasoline engine.

The particular difficulties in achieving effective control of deposits in a direct injection spark ignition gasoline engine are known in the art. For example they are explained in WO 01/42399, U.S. Pat. Nos. 7,112,230, 7,491,248 and WO 03/78553.

Even though fuel compositions and additives have been proposed for controlling deposits in each of the regimes described above, such difficulties show that there is a continuing need for fuel compositions which are effective in either or both of direct injection spark ignition gasoline engines and/or spark ignition gasoline engines without direct injection.

Many different types of compounds are known in the art for use as detergent additives in fuel oil compositions, for the control of deposits in engines.

The present inventors have developed novel quaternary ammonium compounds that are useful as additives in fuel and lubricating compositions.

According to a first aspect of the present invention there is provided a quaternary ammonium salt of formula (I):

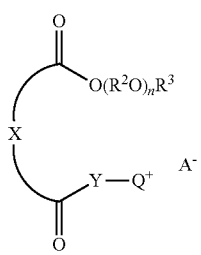

(I)

wherein X is a linking group, Y is O, NH or $NR^1$ wherein $R^1$ is H or an optionally substituted hydrocarbyl group; $Q^+$ is a moiety that includes a quaternary ammonium cation; K is an anion; $R^2$ is an optionally substituted alkylene group; $R^3$ is hydrogen or an optionally substituted hydrocarbyl group; and n is 0 or a positive integer; provided that n is not 0 when $R^3$ is hydrogen.

BRIEF DESCRIPTION OF THE DRAWING

FIG. 1 is a graph showing the test results of fuel compositions of this disclosure.

DETAILED DESCRIPTION

The present invention relates to quaternary ammonium salts and methods and uses relating thereto. This may be referred to herein as "the quaternary ammonium salt" or "the quaternary ammonium compound".

The compound of formula (I) includes a linking group X. In some embodiments X may include one or more carboxylic acid moieties By carboxylic acid moiety we mean to include carboxylic acids groups COOH and groups derived there from, for example esters or amides. In embodiments in which X includes one or more carboxylic acid moieties the quaternary ammonium salt of the invention may be prepared from a polycarboxylic acid having more than two carboxylic acid groups, for example pyromellitic acid.

In preferred embodiments X does not include a carboxylic acid moiety and the quaternary ammonium salt is suitably prepared from a dicarboxylic acid or an anhydride thereof.

Suitably X is an optionally substituted alkylene or arylene group as is further defined herein.

Preferably the quaternary ammonium salt of the invention is a diester or an ester/amide of a dicarboxylic acid.

Suitably the quaternary ammonium salt of the present invention is prepared by reacting:
(a) an optionally substituted dicarboxylic acid or anhydride thereof; with
(b) an alcohol of formula $R^3(OR^2)_nOH$;
(c) a reactive alcohol or amine including a tertiary amino group; and
(d) a quaternising agent.

Component (a) may be first reacted with component (b), then component (c) and finally component (d). Alternatively component (a) may be reacted first with component (c), then component (b), and then component (d).

In preferred embodiments component (a) is first reacted with component (b) and then with component (c).

The quaternary ammonium salt of the present invention is suitably prepared from a (a) hydrocarbyl substituted dicarboxylic acid or anhydride thereof.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:
(i) hydrocarbon groups, that is, aliphatic (which may be saturated or unsaturated, linear or branched, e.g., alkyl or alkenyl), alicyclic (e.g., cycloalkyl, cycloalkenyl) substituents, and aromatic (including aliphatic- and alicyclic-substituted aromatic) substituents, as well as cyclic substituents wherein the ring is completed through another portion of the molecule (e.g., two substituents together form a ring);
(ii) substituted hydrocarbon groups, that is, substituents containing non-hydrocarbon groups which, in the context of this invention, do not alter the predominantly hydrocarbon nature of the substituent (e.g., halo (e.g. chloro, fluoro or bromo), hydroxy, alkoxy (e.g. $C_1$ to $C_4$ alkoxy), keto, acyl, cyano, mercapto, amino, amido, nitro, nitroso, sulfoxy, nitryl and carboxy);
(iii) hetero substituents, that is, substituents which, while having a predominantly hydrocarbon character, in the context of this invention, contain other than carbon in a ring or chain otherwise composed of carbon atoms. Heteroatoms include sulphur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

In this specification, unless otherwise stated references to optionally substituted alkyl groups may include aryl-substituted alkyl groups and references to optionally-substituted aryl groups may include alkyl-substituted or alkenyl-substituted aryl groups.

The additive of the present invention is prepared from a hydrocarbyl substituted dicarboxylic acid or anhydride thereof.

Suitable dicarboxylic acids include maleic acid, glutaric acid, fumaric acid, oxalic acid, malonic acid, pimelic acid, suberic acid, adipic acid, phthalic acid, succinic acid, azelaic acid, sebacic acid and dimerised fatty acids.

In some embodiments the additive is prepared from a dimerised fatty acid. Such compounds are formed from the dimerization of unsaturated fatty acids, for example unsaturated fatty acids having 6 to 50, suitably 8 to 40, preferably 10 to 36, for example 10 to 20 carbon atoms, or 16 to 20 carbon atoms.

Such dimerised fatty acids may have 12-100 carbon atoms, preferably 16-72 carbon atoms such as 20-40 carbon atoms for example 32-40 carbon atoms.

These compounds are well known in the art, particularly for their use as corrosion inhibitors. Particularly preferred dimerised fatty acids are mixtures of C36 dimer acids such as those prepared by dimerising oleic acid, linoleic acid and mixtures comprising oleic and linoleic acid, for example, tall oil fatty acids.

The quaternary ammonium compound of formula (I) includes a linking group X. Preferably X includes a hydrocarbyl substituent. Preferably X is an optionally substituted arylene group or an optionally substituted alkylene group.

In some embodiments the quaternary ammonium salt is prepared from phthalic acid or an anhydride thereof, having the formula (A1) or (A2):

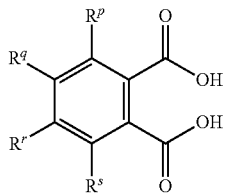

(A1)

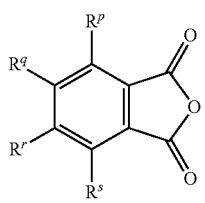

(A2)

wherein each of $R^p$, $R^q$, $R^r$ and $R^s$ is independently hydrogen or an optionally substituted hydrocarbyl group.

Preferably each is hydrogen or an optionally substituted alkyl or alkenyl group. Preferably three of $R^p$, $R^q$, $R^r$ and $R^s$ are hydrogen and the other is an optionally substituted $C_1$ to $C_{500}$ alkyl or alkenyl group, preferably a $C_2$ to $C_{100}$ alkyl or alkenyl group, preferably a $C_6$ to $C_{60}$ alkyl or alkenyl group, preferably a $C_8$ to $C_{40}$ alkyl or alkenyl group, more preferably a $C_{10}$ to $C_{36}$ alkyl or alkenyl group, preferably a $C_{12}$ to $C_{22}$ alkyl or alkenyl group, suitably a $C_{16}$ to $C_{28}$ alkyl or alkenyl group, for example a $C_{20}$ to $C_{24}$ alkyl or alkenyl group. The alkyl or alkenyl group may be straight chain or branched. Preferably $R^p$, $R^q$ and $R^s$ are hydrogen and $R^r$ is an optionally substituted alkyl or alkenyl group.

X is preferably an optionally substituted hydrocarbylene group. Preferably X is an optionally substituted alkylene or arylene group. Preferably X is an optionally substituted alkylene group. Preferably X is a substituted alkylene group.

Suitably X is an alkyl or alkenyl substituted alkylene group.

Preferably X is an alkyl substituted alkylene group.

Preferably X is an alkyl substituted alkylene group wherein the alkylene group was 1 to 10, preferably 1 to 6, suitably 1 to 4, preferably 2 or 3, and most preferably 2 carbon atoms in the alkylene chain.

In some preferred embodiments X is $CH_2CHR^4$ or $CHR^4CH_2$ wherein $R^4$ is an optionally substituted hydrocarbyl group.

Preferably the quaternary ammonium salt of the present invention is prepared from an optionally substituted succinic acid or anhydride thereof of formula (A3) or (A4):

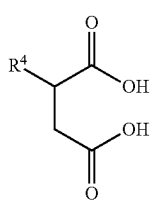

(A3)

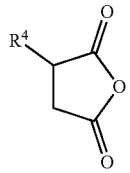

(A4)

wherein $R^4$ is hydrogen or an optionally substituted hydrocarbyl group. Preferably $R^4$ is an optionally substituted alkyl or alkenyl group.

In some embodiments $R^4$ is an optionally substituted $C_1$ to $C_{500}$ alkyl or alkenyl group, preferably a $C_2$ to $C_{100}$ alkyl or alkenyl group, preferably a $C_6$ to $C_{60}$ alkyl or alkenyl group, preferably a $C_8$ to $C_{40}$ alkyl or alkenyl group, more preferably a $C_{10}$ to $C_{38}$ alkyl or alkenyl group, preferably a $C_{16}$ to $C_{36}$ alkyl or alkenyl group, suitably a $C_{18}$ to $C_{32}$ alkyl or alkenyl group.

$R^4$ may be substituted with one or more groups selected from halo (e.g. chloro, fluoro or bromo), nitro, hydroxy, mercapto, sulfoxy, amino, nitryl, acyl, carboxy, alkyl (e.g. $C_1$ to $C_4$ alkyl), alkoxyl (e.g. $C_1$ to $C_4$ alkoxy), amido, keto, sulfoxy and cyano.

Preferably $R^4$ is an unsubstituted alkyl or alkenyl group. The substituted succinic acid or anhydrides may suitably be prepared by reacting maleic anhydride with an alkene.

In some embodiments the $R^4$ has a molecular weight of from 100 to 5000, preferably from 300 to 4000, suitably from 450 to 2500, for example from 500 to 2000 or from 600 to 1500.

In some embodiments the substituted succinic acid or anhydride thereof may comprise a mixture of compounds including groups $R^4$ of different lengths. In such embodiments any reference to the molecular weight of the group $R^4$ relates to the number average molecular weight for the mixture.

In some embodiments $R^4$ is a polyisobutenyl group, preferably having a number average molecular weight of from 100 to 5000, preferably from 200 to 2400, suitably from 220 to 1400.

In some embodiments $R^4$ is an alkyl or alkenyl group having 6 to 40 carbon atoms, preferably 10 to 38 carbon atoms, more preferably 16 to 36 carbon atoms, suitably 18 to 26 carbon atoms, for example 20 to 24 carbon atoms.

In some embodiments $R^4$ may be the residue of an internal olefin. In such embodiments the compound of formula (A3) or (A4) is suitably obtained by the reaction of maleic acid with an internal olefin.

An internal olefin as used herein means any olefin containing predominantly a non-alpha double bond that is a beta or higher olefin. Preferably such materials are substantially completely beta or higher olefins, for example containing less than 10% by weight alpha olefin, more preferably less than 5% by weight or less than 2% by weight. Typical internal olefins include Neodene 151810 available from Shell.

Internal olefins are sometimes known as isomerised olefins and can be prepared from alpha olefins by a process of isomerisation known in the art, or are available from other sources. The fact that they are also known as internal olefins reflects that they do not necessarily have to be prepared by isomerisation.

In some especially preferred embodiments the quaternary ammonium salt of the present invention is prepared from a succinic acid or anhydride having a $C_{10}$ to $C_{30}$, preferably a $C_{20}$ to $C_{24}$ alkyl or alkenyl group.

The quaternary ammonium salt of the present invention may be a compound of formula (IIA) or (IIB):

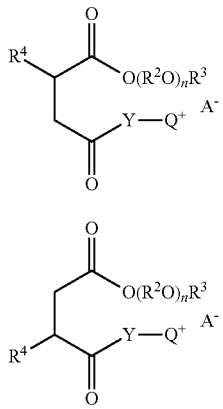

(IIA)

(IIB)

Such a compound may be prepared by reaction with (b) an alcohol of formula $HO(R^2O)_nR^3$.

Suitably n is from 0 to 30, preferably from 1 to 20, suitably from 1 to 16; $R^2$ is an alkylene group having 1 to 12, preferably 1 to 6, more preferably 2 or 3 carbon atoms; and $R^3$ is hydrogen or a $C_1$ to $C_{40}$, preferably a $C_6$ to $C_{30}$, more preferably $C_{10}$ to $C_{20}$ alkyl group; provided n is not 0 when $R^3$ is hydrogen.

$R^3$ is an optionally substituted hydrocarbyl group.

In some embodiments n is 0 and the additive of the invention may be formed from an alcohol of formula $R^3OH$.

In such embodiments $R^3$ is suitably an optionally substituted alkyl, alkenyl or aryl group, preferably having from 1 to 60, preferably from 10 to 40 carbon atoms. Preferably $R^3$ is an optionally substituted alkyl group. In some embodiments $R^3$ is a hydroxy substituted alkyl group.

In some preferred embodiments $R^3$ is an unsubstituted alkyl group. The alkyl group may be straight chained or branched. In some embodiments $R^3$ is an optionally substituted alkyl group having 4 to 40, preferably 6 to 30, more preferably 10 to 20 carbon atoms.

In some embodiments n is 0 and component (b) used to prepare the quaternary ammonium salt is a $C_6$ to $C_{36}$, preferably a $C_{10}$ to $C_{30}$, more preferably a $C_{10}$ to $C_{20}$ optionally substituted alcohol.

In one embodiment component (b) is tetradecanol.

In some embodiments n is 0 and component (b) is an alcohol selected from benzyl alcohol, tetradecanol, butanol, 2-butanol, isobutanol, octanol, 2-ethylhexanol, hexanol, cyclohexanol, cyclooctanol, 2-propylheptanol, isopropanol and 2-ethyl-1-butanol.

In some embodiments n is 0 and component (b) is butanol or 2-ethylhexanol, suitably butanol.

In some embodiments n is not 0 and the quaternary ammonium salt may suitably be formed from an alcohol of formula $HO(R^2O)_nR^3$.

$R^3$ is hydrogen or an optionally substituted hydrocarbyl group.

When $R^3$ is hydrogen component (b) which may be used to prepare the quaternary ammonium salt may be an alkylene glycol or a polyalkylene glycol.

When $R^3$ is not hydrogen, component (a) may be reacted with an alkylene glycol or polyalkylene glycol which is subsequently reacted to form an ether or a compound of formula $HO(R^2O)_nR^3$ may be reacted with component (a).

$R^2$ is an optionally substituted alkylene group. In some embodiments $R^2$ is a hydroxyl substituted alkylene group. Such a group may have 1, 2 or more hydroxyl groups.

For example in some embodiments the additive may be prepared from glycerol, penterythritol or trimethylolpropane.

Preferably $R^2$ is an unsubstituted alkylene group.

Preferably $R^2$ is an optionally substituted alkylene group having 1 to 50 carbon atoms, preferably 1 to 40 carbon atoms, preferably 1 to 30 carbon atoms, more preferably 1 to 20 carbon atoms, suitably 1 to 10 carbon atoms, for example 2 to 6 or 2 to 4 carbon atoms.

Preferably $R^2$ is an unsubstituted alkylene group having 1 to 50 carbon atoms, preferably 1 to 20, more preferably 1 to 10, suitably 2 to 6, for example 2 to 4 carbon atoms. $R^2$ may be straight chained or branched.

Suitably $R^2$ may be an ethylene, propylene, butylene, pentylene, or hexylene group. When R has more than 2 carbon atoms any isomer may be present. Preferably $R^2$ is an ethylene or a propylene group, most preferably a propylene group.

In some embodiments in which n is 1, $R^2$ may be a group of formula $(CH_2)_x$ wherein x is from 2 to 12, preferably from 2 to 6.

In some preferred embodiments $R^2$ is preferably $CR^aR^bCR^cR^d$ and the alcohol (b) has the formula $H—(OCR^aR^bCR^cR^d)_nOR^3$ wherein each of $R^a$, $R^b$, $R^c$ and $R^d$ is independently hydrogen or an optionally substituted alkyl group. Preferably each $R^a$, $R^b$, $R^c$ and $R^d$ is independently selected from hydrogen or an optionally substituted alkyl group having 1 to 20, preferably 1 to 12, more preferably 1 to 4, for example 1 to 2 carbon atoms.

Preferably each of $R^a$, $R^b$, $R^c$ and $R^d$ is independently selected from hydrogen and an unsubstituted alkyl group, preferably having 1 to 20 carbon atoms, suitably 1 to 12 carbon atoms, preferably 1 to 4 atoms, for example 1 or 2 carbon atoms. Preferably at least two of $R^a$, $R^b$, $R^c$ and $R^d$ is hydrogen, more preferably at least three of $R^a$, $R^b$, $R^c$ and $R^d$ is hydrogen.

In some embodiments $R^a$, $R^b$, $R^c$ and $R^d$ are all hydrogen and R is an ethylene group $CH_2CH_2$.

In some embodiments three of $R^a$, $R^b$, $R^c$, and $R^d$ is hydrogen and the other is an unsubstituted alkyl group having 1 to 12, preferably 1 to 4, suitably 1 to 2, and most preferably 1 carbon atoms.

In some embodiments the alcohols (b) used to prepare the quaternary ammonium compounds of the present invention are prepared from epoxides, preferably terminal epoxides.

$R^2$ may comprise a mixture of isomers. For example when $R^2$ is propylene, the polyhydric alcohol may include moieties —$CH_2CH(CH_3)$— and —$CH(CH_3)CH_2$— in any order within the chain.

$R^2$ may comprise a mixture of different groups for example ethylene, propylene or butylene units. Block copolymer units are preferred in such embodiments.

$R^2$ is preferably an ethylene, propylene or butylene group. $R^2$ may be an n-propylene or n-butylene group or an isopropylene or isobutylene group. For example R may be —$CH_2CH_2$—, —$CH_2CH(CH_3)$—, —$CH_2C(CH_3)_2$, —$CH(CH_3)CH(CH_3)$— or —$CH_2CH(CH_2CH_3)$—.

Preferably $R^2$ is ethylene or propylene. More preferably $R^2$ is —$CH_2CH_2$— or —$CH(CH_3)CH_2$—. Most preferably R is —$CH(CH_3)CH_2$—.

In some embodiments n is at least 1. Preferably n is from 1 to 100, preferably from 1 to 50, more preferably from 1 to 30, more preferably from 1 to 24, preferably from 1 to 20, suitably from 1 to 16, preferably from 1 to 14.

In some embodiments n is from 4 to 10, for example from 6 to 8.

In some embodiments n is from 1 to 6, suitably from 2 to 5, for example 3 or 4.

In some embodiments n is from 8 to 16, for example from 11 to 14.

In some embodiments the quaternary ammonium salt of the present invention is formed from a polyhydric alcohol of formula $HO(R^2O)_nH$ or an ether thereof formula $HO(R^2O)_nR^3$.

In some embodiments the polyhydric alcohol may be a polypropylene glycol having a number average molecular weight of 425.

In some embodiments the polyhydric alcohol may be selected from triethylene glycol, tetraethyelene glycol, propylene glycol, dipropylene glycol and tripropylene glycol.

In some embodiments the polyhydric alcohol may be a polypropylene glycol having a number average molecular weight of 725.

The skilled person will appreciate that commercial sources of alcohols of formula $H-(OR^2)_n-OH$ will often contain mixtures of compounds, for example in which n may be between 6 and 10.

Commercial sources of substituted succinic acids and anhydrides may also contain mixtures of compounds, for example including different compounds with substituents having 20 to 24 carbon atoms.

In some preferred embodiments $R^3$ is hydrogen.

In some embodiments $R^3$ is not hydrogen, n is not 0 and the additive of the invention is prepared from an ether of a polyhydric alcohol, for example an ether of a polyethylene glycol, a polypropylene glycol, triethylene glycol, tetraethylene glycol, propylene glycol, dipropylene glycol or tripropylene glycol.

In some embodiments in which n is not 0, $R^3$ is an optionally substituted alkyl, alkenyl or aryl group, suitably an optionally substituted alkyl or alkenyl group. Preferably $R^3$ has from 4 to 50 carbon atoms, preferably 4 to 40 carbon atoms, more preferably from 10 to 30 carbon atoms. $R^3$ may be straight chain or branched. Preferably $R^3$ is straight chain.

In some embodiments $R^3$ is a substituted alkyl or alkenyl group, suitably a substituted alkyl group. Suitably substituents are hydroxy and ester groups.

Suitably $R^3$ is an unsubstituted alkyl or alkenyl group. Preferably $R^3$ is an alkyl group, preferably an unsubstituted alkyl group.

Suitably $R^3$ is selected from hydrogen, and an alkyl group having from 1 to 40, preferably 6 to 30, more preferably 10 to 20 carbon atoms.

In some embodiments n is from 10 to 40, preferably 15 to 30, more preferably 20 to 25; $R^2$ is ethylene or propylene, most preferably propylene; and $R^3$ is a $C_6$ to $C_{30}$, preferably a $C_{10}$ to $C_{20}$ alkyl group.

Y is selected from O, NH and $NR^1$ wherein $R^1$ is an optionally substituted hydrocarbyl group. $R^1$ is suitably an optionally substituted alkyl or alkenyl group, preferably having 1 to 30, preferably 1 to 20, more preferably 1 to 10. Suitably 1 to 6, for example 1 to 4 atoms.

In one preferred embodiment $R^1$ is methyl.

Preferably Y is O or NH. Most preferably Y is NH.

$Q^+$ is a moiety that includes a quaternary ammonium cation. Suitably $Q^+$ is a group having the formula:

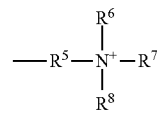

wherein $R^5$ is an optionally substituted alkylene, arylene or alkenylene group and each of $R^6$, $R^7$ and $R^8$ is independently an optionally substituted hydrocarbyl group.

Preferably $R^5$ is an optionally substituted alkylene group, preferably having 1 to 40, preferably 1 to 30, more preferably 1 to 20, suitably 1 to 10, for example 1 to 6 carbon atoms. Most preferably $R^5$ is a propylene group.

$R^6$ is an optionally substituted hydrocarbyl group. Preferably $R^6$ is an optionally substituted alkyl, alkenyl or aryl group. More preferably $R^6$ is an optionally substituted alkyl or alkenyl group, preferably an alkyl group. Most preferably $R^6$ is an unsubstituted alkyl group. Suitably $R^6$ has from 1 to 40 carbon atoms, preferably 1 to 30, more preferably 1 to 20, suitably 1 to 10, for example 1 to 6 carbon atoms. Preferably $R^6$ is a $C_1$ to $C_4$ alkyl group. Most preferably $R^6$ is methyl.

$R^7$ is an optionally substituted hydrocarbyl group. Preferably $R^7$ is an optionally substituted alkyl, alkenyl or aryl group. More preferably $R^7$ is an optionally substituted alkyl or alkenyl group, preferably an alkyl group. Most preferably $R^7$ is an unsubstituted alkyl group. Suitably $R^6$ has from 1 to 40 carbon atoms, preferably 1 to 30, more preferably 1 to 20, suitably 1 to 10, for example 1 to 6 carbon atoms. Preferably $R^7$ is a $C_1$ to $C_4$ alkyl group. Most preferably $R^7$ is methyl.

$R^8$ is an optionally substituted hydrocarbyl group. Preferably $R^8$ is an optionally substituted alkyl, alkenyl or aryl group. Preferably $R^8$ is an optionally substituted alkyl or alkenyl group. Preferably $R^8$ is an optionally substituted alkyl or alkenyl group having 1 to 40 carbon atoms, preferably 1 to 30, more preferably 1 to 20, suitably 1 to 10, for example 1 to 6 carbon atoms. Preferably $R^8$ is an unsubstituted alkyl group or a hydroxy substituted alkyl group.

$R^8$ is suitably provided by a quaternising agent.

The quaternary ammonium compounds of the present invention may be prepared by any suitable method. Such methods are known to the person skilled in the art.

Suitably the quaternary ammonium salts of the present invention are prepared by the reaction of a tertiary amine of formula (III) with a quaternising agent.

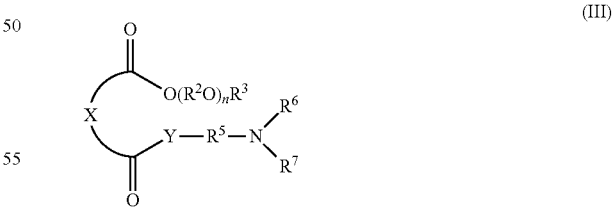

(III)

The compound of formula (III) is suitably prepared by the reaction of a hydrocarbyl substituted dicarboxylic acid or anhydride thereof with an alcohol of formula $HO(R^2O)_nR^3$ and a tertiary amine of formula $R^6R^7NR^5YH$; wherein $R^2$ is an optionally substituted alkylene group, $R^3$ is hydrogen or an optionally substituted hydrocarbyl group, $R^5$ is an optionally substituted alkylene, arylene or alkenylene group; X is O or NR'; $R^6$ and $R^7$ is each an optionally substituted hydrocarbyl group; $R^1$ is hydrogen or an optionally substituted hydrocarbyl group; and n is 0 or positive integer provided that when $R^3$ is hydrogen n is not 0.

Preferably each of $R^1$, $R^2$, $R^3$, $R^5$, $R^6$ and $R^7$ are as previously defined herein.

The compound of formula (III) may suitably be provided by reacting (a) a hydrocarbyl substituted dicarboxylic acid or anhydride thereof with (b) an alcohol of formula $R^3(OR^2)_nOH$ and (c) a reactive alcohol or amine including a tertiary amino group.

In some preferred embodiments component (c) is a reactive alcohol including a tertiary amino group.

The reactive alcohol or amine or alcohol including a tertiary amino group suitably have the formula $R^6R^7NR^5YH$.

Suitable reactive amines including a tertiary amino group include N,N-dimethyl-1,3-diaminopropane, N,N-diethyl-1,3-diaminopropane, N,N-dimethylethylenediamine, N,N-diethylethylenediamine, N,N-dibutylethylenediamine and combinations thereof.

Suitable reactive alcohols including a tertiary amino group include triisopropanolamine, 1-[2-hydroxyethyl]piperidine, 2-[2-(dimethylamine)ethoxy]-ethanol, N-ethyldiethanolamine, N-methyldiethanolamine, N-butyldiethanolamine, N,N-diethylaminoethanol, N,N-dimethylaminoethanol, 2-dimethylamino-2-methyl-1-propanol, dimethyl amino propanol and combinations thereof.

Especially preferred compounds for use as component (c) are dimethylaminopropylamine and dimethylaminopropanol. Most preferred is dimethylaminopropanol.

The quaternary ammonium salts of the present invention may be prepared by reaction of a tertiary amine of formula (III) with a quaternising agent selected from dialkyl sulfates, benzyl halides, hydrocarbyl substituted carbonates, alkyl halides, alkyl sulfonates, sultones, hydrocarbyl substituted phosphates, hydrocarbyl substituted borates, alkyl nitrites, alkyl nitrates, hydroxides, N-oxides or mixtures thereof, followed by an anion exchange reaction.

However in preferred embodiments the quaternary ammonium salt of the present invention is prepared by the reaction of a tertiary amine of formula (III) with a quaternising agent selected from:
(i) an ester of formula $R^9COOR^8$;
(ii) a carbonate compound of formula $R^{10}OCOOR^8$ and then a carboxylic acid of formula $R^9COOH$; and
(iii) an epoxide in combination with an acid, preferably a carboxylic acid of formula $R^9COOH$;
wherein $R^8$ is as previously defined herein and $R^9$ is an optionally substituted hydrocarbyl group.

Suitably the anion $A^-$ shown in formula (I) is $R^9COO^-$; wherein $R^9$ is an optionally substituted hydrocarbyl group.

In one embodiment the quaternising agent is (i) an ester of formula $R^9COOR^8$.

In such embodiments $R^8$ is a $C_1$ to $C_7$ alkyl group and $R^9$ is the residue of a carboxylic acid selected from a substituted aromatic carboxylic acid, an α-hydroxycarboxylic acid and a polycarboxylic acid.

In some preferred embodiments the quaternising agent is an ester of a substituted aromatic carboxylic acid and thus $R^9$ is a substituted aryl group.

Especially preferred compounds of this type are lower alkyl esters of salicylic acid such as methyl salicylate, ethyl salicylate, n and i-propyl salicylate, and butyl salicylate, preferably methyl salicylate.

In some embodiments the quaternising agent is an ester of an α-hydroxycarboxylic acid.

Compounds of this type suitable for use herein are described in EP 1254889.

A preferred compound of this type is methyl 2-hydroxyisobutyrate.

In some embodiments the quaternising agent is an ester of a polycarboxylic acid. In this definition we mean to include dicarboxylic acids and carboxylic acids having more than 2 acidic moieties.

One especially preferred compound of this type is dimethyl oxalate.

The ester quaternising agent may be selected from an ester of a carboxylic acid selected from one or more of oxalic acid, phthalic acid, tartaric acid, salicylic acid, maleic acid, malonic acid, citric acid, nitrobenzoic acid, aminobenzoic acid and 2,4,6-trihydroxybenzoic acid.

Preferred ester quaternising agents include dimethyl oxalate, methyl 2-nitrobenzoate, dimethylphthalate, dimethyltartrate and methyl salicylate.

In some embodiments the quaternary ammonium salts are prepared by reacting a compound of formula (III) with (ii) a carbonate of formula $R^{10}OCOOR^8$ and then with a carboxylic acid of formula $R^9COOH$. $R^8$ is as defined above. $R^{10}$ is preferably an optionally substituted alkyl alkenyl or aryl group having up to 30 carbon atoms. Preferably $R^9$ is an optionally substituted alkyl group. Preferably $R^{10}$ is an alkyl group having up to 24 carbon atoms, preferably up to 20 carbon atoms, suitably up to 16 carbon atoms, preferably up to 12 carbon atoms, suitably up to 8, for example up to 6 or up to 4 carbon atoms.

Preferably $R^{10}$ is an unsubstituted alkyl group. In one embodiment $R^{10}$ may be the same or different to $R^8$. Preferably $R^{10}$ is the same as $R^8$. Preferred carbonates are diethyl carbonate and dimethyl carbonate. Dimethyl carbonate is especially preferred. Once the tertiary amine has been reacted with a carbonate quaternising group the resulting salt is then reacted with a carboxylic acid of formula $R^9COOH$ to provide a compound of the first aspect.

The carboxylic acid of formula $R^9COOH$ may be a very small simple molecule. In some embodiments it may be a simple fatty acid compound. However it may also be a more complex molecule including additional acid functional groups.

Examples of suitable small simple acids include formic acid, acetic acid, propionic acid and butyric acid.

Examples of suitable fatty acids include caprylic acid, capris acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, arachidonic acid, eicosapentaenoic acid, erucic acid, undecylenic acid and docosahexenoic acid.

Suitable complex acids include optionally substituted phthalic acid and succinic acid derivatives.

In embodiments in which the acid includes more than one acid functional group the further groups may be present as the free acid or the ester. Where there is more than one free acid group there is suitably an equivalent number of cations.

In some preferred embodiments the quaternising agent is (iii) the combination of an epoxide and an acid. Any suitable organic or inorganic acid may be used. Preferably the acid is a carboxylic acid of formula $R^9COOH$.

One especially preferred acid for use herein is acetic acid.

When the quaternising agent is an (i) an ester of formula $R^9COOR^8$ or (ii) a carbonate of formula $R^{10}OCOOR^8$ and an acid of formula $R^9COOH$, $R^8$ is preferably an alkyl group, preferably methyl or ethyl, most preferably methyl.

When the quaternising agent is (iii) an epoxide in combination with an acid $R^8$ is suitably $CH_2CHOHR^{11}$ wherein $R^{11}$ is hydrogen or an optionally substituted hydrocarbyl group.

Preferably $R^{11}$ is hydrogen or an optionally substituted alkyl or aryl group. $R^{11}$ may have 1 to 40 carbon atoms, suitably 1 to 30, preferably 1 to 20 carbon atoms.

Preferably $R^{11}$ is hydrogen, phenyl or a $C_1$ to $C_{12}$ alkyl group. The alkyl group may include an ester or an ether functional group.

$R^{11}$ may be hydrogen or a $C_1$ to $C_8$, preferably a $C_1$ to $C_6$; more preferably a $C_1$ to $C_4$, for example a $C_2$ or $C_3$ alkyl group.

Preferred epoxides for use as quaternising agents in combination with an acid include ethylene oxide, propylene oxide, butylene oxide, pentylene oxide, hexylene oxide and heptylene oxide. These may be provided as appropriate in any isomeric form or as a mixture of isomers. Also useful are glycidyl ether compounds, for example isopropyl glycidyl ether.

Suitably the epoxide for use as a quaternising agents in combination with an acid may be selected from styrene oxide, ethylene oxide, propylene oxide, butylene oxide, epoxyhexane, octene oxide, stilbene oxide, 2-ethylhexyl glycidyl ether, isopropyl glycidyl ether, 1,2-epoxydodecane and other alkyl and alkenyl epoxides having 2 to 50 carbon atoms.

Especially preferred epoxides are 1,2-epoxy butane and isopropyl glycidyl ether.

Some preferred epoxides are 1,2-epoxydodecane, styrene oxide and butylene oxide, suitably in combination with acetic acid.

The quaternising ammonium compound of the invention of formula (I) may include any anion $A^-$.

$A^-$ may be a polyvalent anion.

Preferred anions are residues of carboxylic acids of formula $R^9COO^-H$. these are suitably as previously defined herein.

In some preferred embodiments $A^-$ is an acetate ion.

In some preferred embodiments X is $CH_2CHR^4$ or $CHR^4CH_2$ wherein $R^4$ is a $C_6$ to $C_{50}$, preferably a $C_{10}$ to $C_{36}$ alkyl group; $R^2$ is ethylene or propylene; n is from 1 to 30, preferably 4 to 20; $R^3$ is hydrogen or $C_4$ to $C_{30}$ alkyl, preferably hydrogen; Y is O or NH, preferably O; $Q^+$ is hydroxyalkyl dialkyl amino alkylene, preferably 2-hydroxybutyl dimethyl amino propylene; and $A^-$ is a carboxylate anion.

In some embodiments the quaternary ammonium compound of the present invention is the reaction product of a succinic acid or anhydride thereof having an alkyl or alkenyl substituent having 6 to 36 carbon atoms; a polyalkylene glycol having a number average molecular weight of 300 to 800 or an ether thereof; a dialkyl aminoalkanol or a dialkylamino alkylamine; and a quaternising agent.

In some embodiments the quaternary ammonium salt additive of the invention is the reaction product of a succinic acid or anhydride thereof having an alkyl or alkenyl substituent having 6 to 36 carbon atoms; a polypropylene glycol (or a $C_1$ to $C_{36}$ alkyl ether thereof) having a number average molecular weight of 300 to 800; a dialkylamino alkanol or a dialkylamino amine; and a quaternising agent.

In some embodiments the quaternary ammonium salt additive of the invention is the reaction product of a succinic acid or anhydride thereof having an alkyl or alkenyl substituent having 6 to 36 carbon atoms; a polyhydric alcohol (or a $C_1$ to $C_{36}$ alkyl ether thereof) selected from ethylene glycol, diethylene glycol, triethylene glycol, tetraethylene glycol, propylene glycol, dipropylene glycol, tripropylene glycol and tetrapropylene glycol; a dialkylamino alkanol or a dialkylamino amine; and a quaternising agent.

In some embodiments the quaternary ammonium salt additive of the invention is the reaction product of a succinic acid or anhydride thereof having an alkyl or alkenyl substituent having 6 to 36 carbon atoms; a polyhydric alcohol (or a $C_1$ to $C_{36}$ alkyl ether thereof) selected from glycerol, pentaerythritol and trimethyolpropane; a dialkylamino alkanol or a dialkylamino amine; and a quaternising agent.

In some embodiments the quaternary ammonium salt additive of the invention is the reaction product of a succinic acid or anhydride thereof having an alkyl or alkenyl substituent having 6 to 36 carbon atoms; a polyethylene glycol (or a $C_1$ to $C_{36}$ alkyl ether thereof) having a number average molecular weight of 200 to 800; a dialkylamino alkanol or a dialkylamino amine; and a quaternising agent.

In some embodiments the quaternary ammonium salt additive of the present invention is the reaction product of a succinic acid or anhydride having an alkyl or alkenyl substitutent having 6 to 36 carbon atoms; a polyethylene or polypropylene glycol (or a $C_1$ to $C_{36}$ alkyl ether thereof) having 4 to 16, preferably 6 to 8 alkoxy groups; a dialkylamino alkanol or a dialkylamino amine; and a quaternising agent.

In some embodiments the quaternary ammonium salt additive of the invention is the reaction product of a polyisobutenyl substituted succinic acid or anhydride thereof having a PIB substituent with a number average molecular weight of 200 to 2500; a polypropylene glycol (or a $C_1$ to $C_{36}$ alkyl ether thereof) having a number average molecular weight of 300 to 800; a dialkylamino alkanol or a dialkylamino amine; and a quaternising agent.

In some embodiments the quaternary ammonium salt additive of the invention is the reaction product of a polyisobutenyl substituted succinic acid or anhydride thereof having a PIB substituent with a number average molecular weight of 200 to 2500; a polyhydric alcohol (or a $C_1$ to $C_{36}$ alkyl ether thereof) selected from ethylene glycol, diethylene glycol, triethylene glycol, tetraethylene glycol, propylene glycol, dipropylene glycol, tripropylene glycol and tetrapropylene glycol; a dialkylamino alkanol or a dialkylamino amine; and a quaternising agent.

In some embodiments the quaternary ammonium salt additive of the invention is the reaction product of a polyisobutenyl substituted succinic acid or anhydride thereof having a PIB substituent with a number average molecular weight of 200 to 2500; a polyhydric alcohol (or a $C_1$ to $C_{36}$ alkyl ether thereof) selected from glycerol, pentaerythritol and trimethyolpropane; a dialkylamino alkanol or a dialkylamino amine; and a quaternising agent.

In some embodiments the quaternary ammonium salt additive of the invention is a the reaction product of polyisobutenyl substituted succinic acid or anhydride thereof having a PIB substituent with a number average molecular weight of 200 to 2500; a polyethylene glycol (or a $C_1$ to $C_{36}$ alkyl ether thereof) having a number average molecular weight of 200 to 800; a dialkylamino alkanol or a dialkylamino amine; and a quaternising agent.

In some embodiments the quaternary ammonium salt additive of the invention is the reaction product of a polyisobutenyl substituted succinic acid or anhydride thereof having a PIB substituent with a number average molecular weight of 200 to 2500; a polyethylene or polypropylene glycol (or a $C_1$ to $C_{36}$ alkyl ether thereof) having 4 to 16, preferably 6 to 8 alkoxy groups; a dialkylamino alkanol or a dialkylamino amine; and a quaternising agent.

The quaternary ammonium salt of formula (I) is suitably prepared from the reaction of:
(a) an optionally substituted dicarboxylic acid or anhydride thereof; with
(b) an alcohol of formula $R^3(OR^2)_nOH$;
(c) a reactive alcohol or amine including a tertiary amino group; and
(d) a quaternising agent.

Suitably the quaternary ammonium salt is prepared from:
(a) an optionally substituted succinic acid or anhydride thereof;
(b) an alcohol of formula $H(OR^2)_nOH$ or $R^3OH$;
(c) a reactive alcohol including a tertiary amino group; and
(d) a quaternising agent.

Preferably $R^2$ is —$CH(CH_3)CH_2$— and $R^3$ is a $C_2$ to $C_{16}$ alkyl group.

Preferably the quaternary ammonium salt is prepared from:
(a) a succinic acid or anhydride thereof substituted with a $C_{20}$ to $C_{24}$ alkyl or alkenyl group;
(b) a polypropylene glycol or butanol;
(c) dimethylaminopropanol; and
(d) a quaternising agent selected from methyl salicylate, dimethyl oxalate and a hydrocarbyl epoxide in combination with an acid.

Most preferably the quaternising agent is methyl salicylate or dimethyl oxalate.

According to a second aspect of the present invention there is provided a composition comprising a quaternary ammonium salt of formula (I):

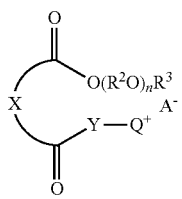

wherein X is a linking group, Y is O, NH or $NR^1$ wherein $R^1$ is H or an optionally substituted hydrocarbyl group; $Q^+$ is a moiety that includes a quaternary ammonium cation; $A^-$ is an anion; $R^2$ is an optionally substituted alkylene group; $R^3$ is hydrogen or an optionally substituted hydrocarbyl group; and n is 0 or a positive integer; provided that n is not 0 when $R^3$ is hydrogen.

Preferred features of the quaternary ammonium salt are as defined in relation to the first aspect.

In some embodiments the composition of the second aspect is an additive composition comprising a quaternary ammonium salt of the first aspect and a diluent or carrier.

The additive composition may be an additive composition for lubricating oil.

Preferably the additive composition is an additive composition for a fuel composition, preferably a gasoline fuel composition.

The quaternary ammonium compound is suitably present in the additive composition in an amount of from 1 to 99 wt %, for example from 1 to 75 wt %.

The additive composition may comprise a mixture of two or more quaternary ammonium compounds of the present invention. In such embodiments the above amounts suitably refer to the total amount of all such compounds present in the composition.

The additive composition may include one or more further additives. These may be selected from further detergents, dispersants, anti-oxidants, anti-icing agents, metal deactivators, lubricity additives, friction modifiers, dehazers, corrosion inhibitors, dyes, markers, octane improvers, anti-valve-seat recession additives, stabilisers, demulsifiers, antifoams, odour masks, conductivity improvers and combustion improvers.

In some preferred embodiments the additive composition includes one or more further nitrogen-containing detergents.

The second aspect of the present invention may provide a fuel or lubricating oil composition comprising a quaternary ammonium salt of the first aspect.

In some embodiments the present invention provides a lubricating composition comprising an oil of lubricating viscosity and as an additive a quaternary ammonium salt of formula (I):

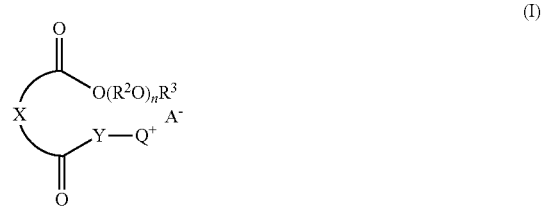

wherein X is a linking group, Y is O, NH or $NR^1$ wherein $R^1$ is H or an optionally substituted hydrocarbyl group; $Q^+$ is a moiety that includes a quaternary ammonium cation; $A^-$ is an anion; $R^2$ is an optionally substituted alkylene group; $R^3$ is hydrogen or an optionally substituted hydrocarbyl group; and n is 0 or a positive integer; provided that n is not 0 when $R^3$ is hydrogen.

In some preferred embodiments the second aspect of the present invention provides a fuel composition comprising as an additive a quaternary ammonium salt of formula (I):

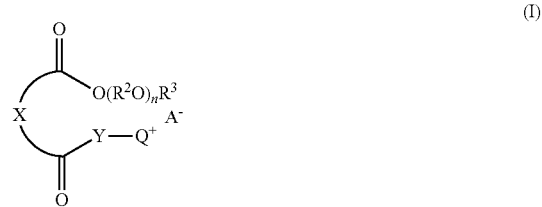

wherein X is a linking group, Y is O, NH or $NR^1$ wherein $R^1$ is H or an optionally substituted hydrocarbyl group; $Q^+$ is a moiety that includes a quaternary ammonium cation; $A^-$ is an anion; $R^2$ is an optionally substituted alkylene group; $R^3$ is hydrogen or an optionally substituted hydrocarbyl group; and n is 0 or a positive integer; provided that n is not 0 when $R^3$ is hydrogen.

The present invention may further provide a method of preparing a fuel composition, the method comprising preparing a quaternary ammonium salt of the first aspect, and mixing the quaternary ammonium salt into the fuel.

The fuel composition of the present invention is preferably a gasoline fuel composition.

Suitably the quaternary ammonium salt additive is present in the gasoline fuel composition in an amount of at least 0.1 ppm, preferably at least 1 ppm, more preferably at least 5 ppm, suitably at least 10 ppm, preferably at least 20 ppm, for example at least 30 ppm or at least 50 ppm.

Suitably the quaternary ammonium salt additive is present in the gasoline fuel composition in an amount of less than 10000 ppm, preferably less than 1000 ppm, preferably less than 500 ppm, preferably less than 300 ppm, for example less than 250 ppm.

In some embodiments the quaternary ammonium salt additive is present in the gasoline fuel composition in an amount of suitably less than 200 ppm, for example less than 150 ppm.

Suitably the quaternary ammonium salt additive is present in the gasoline fuel in an amount of from 80 to 130 ppm.

In this specification any reference to ppm is to parts per million by weight.

The gasoline fuel compositions of the present invention may comprise a mixture of two or more quaternary ammonium salt additives. In such embodiments the above amounts refer to the total amounts of all such additives present in the composition.

The use of mixtures may arise due to the availability of starting materials or a particular mixture may be deliberately selected to use in order to achieve a benefit. For example, a particular mixture may lead to improvements in handling, a general improvement in performance or a synergistic improvement in performance.

In this specification any reference to "an additive" or "the additive" of the invention includes embodiments in which a single additive compound is present and embodiments in which two or more additive compounds are present. In embodiments in which two or more compounds are present the mixtures may be present due to a mixture of starting materials being used to prepare the additive compounds (e.g. a mixture of polyhydric alcohols and/or a mixture of polycarboxylic acids and/or a mixture of tertiary amines and/or a mixture of quaternising agents). Alternatively and/or additionally two or more pre-formed compounds of formula (I) may be mixed into a composition, for example a fuel or lubricating composition.

The quaternary ammonium additives may be added to gasoline fuel at any convenient place in the supply chain. For example, the additives may be added to fuel at the refinery, at a distribution terminal or after the fuel has left the distribution terminal. If the additive is added to the fuel after it has left the distribution terminal, this is termed an aftermarket application. Aftermarket applications include such circumstances as adding the additive to the fuel in the delivery tanker, directly to a customer's bulk storage tank, or directly to the end user's vehicle tank. Aftermarket applications may include supplying the fuel additive in small bottles suitable for direct addition to fuel storage tanks or vehicle tanks.

The second aspect of the present invention preferably relates to a gasoline fuel composition.

By the term "gasoline", it is meant a liquid fuel for use with spark ignition engines (typically or preferably containing primarily or only C4-C12 hydrocarbons) and satisfying international gasoline specifications, such as ASTM D-439 and EN228. The term includes blends of distillate hydrocarbon fuels with oxygenated components such as alcohols or ethers for example methanol, ethanol, butanol, methyl t-butyl ether (MTBE), ethyl t-butyl ether (ETBE), as well as the distillate fuels themselves.

In some preferred embodiments, the quaternary ammonium salt additives may be used without additional components. In other preferred embodiments, the quaternary ammonium salt additive (i) is used with one or more additional components (ii) selected from:
  a) carrier oils
  b) acylated nitrogen compounds which are the reaction product of a carboxylic acid-derived acylating agent and an amine
  c) hydrocarbyl-substituted amines wherein the hydrocarbyl substituent is substantially aliphatic and contains at least 8 carbon atoms
  d) mannich base additives comprising nitrogen-containing condensates of a phenol, aldehyde and primary or secondary amine
  e) aromatic esters of a polyalkylphenoxyalkanol
  f) quaternary ammonium salts.

Preferably the ratio of the quaternary ammonium salt additive (i) to additional components (ii) when present, is 1:100 to 100:1, preferably 1:50:50:1, preferably 1:15 to 20:1 preferably 1:15 to 10:1 preferably 1:10 to 10:1 preferably 1:5 to 5:1.

Preferably the ratio of the quaternary ammonium salt additive (i) to carrier oil a) when present, is 1:100 to 100:1, preferably 1:50:50:1, preferably 1:15 to 20:1 preferably 1:15 to 10:1 preferably 1:10 to 10:1 preferably 1:5 to 5:1, preferably 1:2 to 2:1.

Preferably the ratio of the quaternary ammonium salt additive (i) to acylated nitrogen additive b) 1:100 to 100:1, preferably 1:50:50:1, preferably 1:15 to 20:1 preferably 1:15 to 10:1 preferably 1:10 to 10:1 preferably 1:5 to 5:1, preferably 1:2 to 2:1.

Preferably the ratio of the quaternary ammonium salt additive (i) to hydrocarbyl substituted amine c) 1:100 to 100:1, preferably 1:50:50:1, preferably 1:15 to 20:1 preferably 1:15 to 10:1 preferably 1:10 to 10:1 preferably 1:5 to 5:1, preferably 1:2 to 2:1.

Preferably the ratio of the quaternary ammonium salt additive (i) to mannich base additives d) when present, is 1:100 to 100:1, preferably 1:50:50:1, preferably 1:15 to 20:1 preferably 1:15 to 10:1 preferably 1:10 to 10:1 preferably 1:5 to 5:1, preferably 1:2 to 2:1.

Preferably the ratio of the quaternary ammonium salt additive (i) to aromatic ester e) 1:100 to 100:1, preferably 1:50:50:1, preferably 1:15 to 20:1 preferably 1:15 to 10:1 preferably 1:10 to 10:1 preferably 1:5 to 5:1, preferably 1:2 to 2:1.

Preferably the ratio of the quaternary ammonium salt additive (i) to quaternary ammonium salt f) 1:100 to 100:1, preferably 1:50:50:1, preferably 1:15 to 20:1 preferably 1:15 to 10:1 preferably 1:10 to 10:1 preferably 1:5 to 5:1, preferably 1:2 to 2:1.

Preferably the ratio of the total of the quaternary ammonium salt additive (i) and components b), c), d) and e) to carrier oil a) when present, is 1:100 to 100:1, preferably 1:50:50:1, preferably 1:15 to 20:1 preferably 1:15 to 10:1 preferably 1:10 to 10:1 preferably 1:5 to 5:1, preferably 1:2 to 2:1.

All ratios are weight ratios on an active basis. The total amount of compound(s) (i) and each compound a)-f) specified in the respective definition is to be taken into account.

a) Carrier Oil

The carrier oil may have any suitable molecular weight. A preferred molecular weight is in the range 500 to 5000.

In one embodiment the carrier oil may comprise an oil of lubricating viscosity. The oil of lubricating viscosity includes natural or synthetic oils of lubricating viscosity, oil derived from hydrocracking, hydrogenation, hydrofinishing, unrefined, refined and re-refined oils, or mixtures thereof. In one embodiment, the oil of lubricating viscosity is a carrier fluid for the dispersant and/or other performance additives.

Natural oils include animal oils, vegetable oils, mineral oils or mixtures thereof. Synthetic oils include a hydrocarbon oil, a silicon-based oil, a liquid ester of phosphorus-containing acid. Synthetic oils may be produced by Fischer-Tropsch reactions and typically may be hydroisomerised Fischer-Tropsch hydrocarbons or waxes.

Oils of lubricating viscosity may also be defined as specified in the American Petroleum Institute (API) Base Oil Interchangeability Guidelines. In one embodiment the oil of lubricating viscosity comprises an API Group I, II, III, IV, V or mixtures thereof, and in another embodiment API Group I, II, III or mixtures thereof.

In another embodiment the carrier oil may comprise a polyether carrier oil.

In a preferred aspect the polyether carrier oil is a mono end-capped polyalkylene glycol. Preferably the end cap is a group consisting of or containing a hydrocarbyl group having up to 30 carbon atoms. More preferably the end cap is or comprises an alkyl group having from 4 to 20 carbon atoms or from 12 to 18 carbon atoms.

The alkyl group may be branched or straight chain. Preferably it is a straight chain group.

Further hydrocarbyl end capping groups include alkyl-substituted phenyl, especially where the alkyl substituent(s) is or are alkyl groups of 4 to 20 carbon atoms, preferably 8 to 12, preferably straight chain.

The hydrocarbyl end capping group may be attached to the polyether via a linker group. Suitable end cap linker groups include an ether oxygen atom (—O—), an amine group (—NH—), an amide group (—CONH—), or a carbonyl group —(C═O)—.

Such end capped polyalkyleneglycols are obtainable by the polymerisation of $C_2$-$C_6$ alkylene oxides either as homopolymers or copolymers containing 4-100 repeat units. Copolymers may be random copolymers or block copolymers.

In a preferred aspect the polyether carrier oil is a mono end-capped polypropylene glycol.

In a preferred embodiment the carrier oil is a polyalkyleneglycol monoether of the formula:

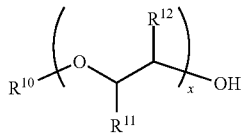

(C1)

where $R^{10}$ is a hydrocarbyl group having from 1 to 30 carbon atoms; $R^{11}$ and $R^{12}$ are each independently hydrogen or lower alkyl having from about 1 to about 6 carbon atoms and each $R^{11}$ and $R^{12}$ is independently selected in each —O—$CHR^{11}$—$CHR^{12}$— unit; and x is an integer of from 5 to 100, preferably 10 to 50, preferably 10 to 30, preferably 10-25, more preferably 12 to 25, more preferably 12 to 20.

In a preferred embodiment $R^{10}$ is a straight chain $C_1$-$C_{30}$ alkyl, preferably $C_4$-$C_{20}$ alkyl, preferably $C_8$-$C_{18}$ alkyl, and more preferably $C_{12}$-$C_{18}$ alkyl or $C_8$-$C_{14}$ alkyl.

In another preferred embodiment $R^{10}$ is an alkylphenyl group preferably an alkylphenyl group, wherein the alkyl moiety is a straight or branched chain alkyl of from about 1 to about 24 carbon atoms.

Preferably, one of $R^{11}$ and $R^{12}$ is lower alkyl of 1 to 4 carbon atoms, and the other is hydrogen. More preferably, one of $R_1$ and $R_2$ is methyl or ethyl, and the other is hydrogen.

In a preferred embodiment the carrier oil is a polypropyleneglycol monoether of the formula:

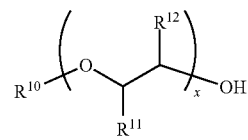

(C2)

where $R^{10}$, $R^{11}$, $R^{12}$ and x are as defined for (C1) above, and in each repeat unit one of $R^{11}$ and $R^{12}$ are hydrogen and the other is methyl.

Such alkyl polypropyleneglycol monoethers are obtainable by the polymerisation of propylene oxide using an aliphatic alcohol, preferably a straight chain primary alcohol of up to 20 carbon atoms, as an initiator. If desired a proportion of the propyleneoxy units, for example up to 50% of the propyleneoxy units by weight, may be replaced by units derived from other $C_2$-$C_6$ alkylene oxides, e.g. ethylene oxide or isobutylene oxide, and are to be included within the term "polypropyleneglycol". Alternatively, the initiator may be a phenol, alkyl phenol, a hydrocarbyl amine or amide, containing 1-30 carbon atoms, preferably a saturated aliphatic or aromatic hydrocarbyl group such as alkyl, phenyl or phenalkyl etc. Preferred initiators include long chain alkanols giving rise to the long chain polypropyleneglycol monoalkyl ethers.

In a further aspect the polyalkyleneglycol may be an ester. In this aspect the carrier oil may be a polypropyleneglycol monoester of the formula

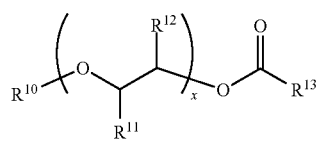

(C3)

where $R^{10}$, $R^{11}$, $R^{12}$ and x are as defined for (C1) above and $R^{13}$ is a $C_1$-$C_{30}$ hydrocarbyl group, preferably an aliphatic hydrocarbyl group, and more preferably $C_1$-$C_{10}$ alkyl.

In another embodiment a polyetheramine may be present.

It is known to those skilled in the art that the class of compounds known as polyetheramines function as deposit control additives. It is common for polyetheramines to be used as detergents and/or as carrier oils. For the purpose of this specification polyetheramines are classed herein as carrier oils.

Suitable hydrocarbyl-substituted polyoxyalkylene amines or polyetheramines employed in the present invention are described in the literature (for example U.S. Pat. Nos. 6,217,624 and 4,288,612) and have the general formula:

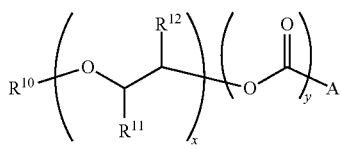 (C4)

or a fuel-soluble salt thereof; $R^{10}$, $R^{11}$, $R^{12}$ and x are as defined for (C1) above; A is amino, N-alkyl amino having about 1 to about 20 carbon atoms in the alkyl group, N,N-dialkyl amino having about 1 to about 20 carbon atoms in each alkyl group, or a polyamine moiety having about 2 to about 12 amine nitrogen atoms and about 2 to about 40 carbon atoms; and y is 0 or 1.

In general, A is amino, N-alkyl amino having from about 1 to about 20 carbon atoms in the alkyl group, preferably about 1 to about 6 carbon atoms, more preferably about 1 to about 4 carbon atoms; N,N-dialkyl amino having from about 1 to about 20 carbon atoms in each alkyl group, preferably about 1 to about 6 carbon atoms, more preferably about 1 to about 4 carbon atoms; or a polyamine moiety having from about 2 to about 12 amine nitrogen atoms and from about 2 to about 40 carbon atoms, preferably about 2 to 12 amine nitrogen atoms and about 2 to 24 carbon atoms. More preferably, A is amino or a polyamine moiety derived from a (poly)alkylene polyamine, including alkylene diamine. Most preferably, A is amino or a polyamine moiety derived from ethylene diamine or diethylene triamine.

The polyetheramines will generally have a molecular weight in the range from about 600 to about 10,000.

Fuel-soluble salts of the compounds of formula I can be readily prepared for those compounds containing an amino or substituted amino group and such salts are contemplated to be useful for preventing or controlling engine deposits. Suitable salts include, for example, those obtained by protonating the amino moiety with a strong organic acid, such as an alkyl- or arylsulfonic acid. Preferred salts are derived from toluenesulfonic acid and methanesulfonic acid.

Other suitable polyetheramines are those taught in U.S. Pat. Nos. 5,089,029 and 5,112,364.

b) Acylated Nitrogen Compounds which are the Reaction Product of a Carboxylic Acid-Derived Acylating Agent and an Amine The carboxylic derived acylating agent may be a hydrocarbyl substituted acylating agent as described for the quaternary ammonium salt(s) (i).

Amines useful for reaction with these acylating agents include the following:

(1) (Poly)alkylene polyamines of the general formula:

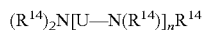

wherein each $R^{14}$ is independently selected from a hydrogen atom, a hydrocarbyl group or a hydroxy-substituted hydrocarbyl group containing up to about 30 carbon atoms, with proviso that at least one $R^{14}$ is a hydrogen atom, n is a whole number from 1 to 10 and U is a C1-18 alkylene group. Preferably each $R^{14}$ is independently selected from hydrogen, methyl, ethyl, propyl, isopropyl, butyl and isomers thereof. Most preferably each $R^{14}$ is ethyl or hydrogen. U is preferably a C1-4 alkylene group, most preferably ethylene.

Specific examples of (poly)alkylene polyamines (1) include ethylenediamine, diethylenetriamine, triethylenetetramine, tetraethylenepentamine, tri(tri-methylene)tetramine, pentaethylenehexamine, hexaethylene-heptamine, 1,2-propylenediamine, and other commercially available materials which comprise complex mixtures of polyamines. For example, higher ethylene polyamines optionally containing all or some of the above in addition to higher boiling fractions containing 8 or more nitrogen atoms etc.

Specific examples of (poly)alkylene polyamines (1) which are hydroxyalkyl-substituted polyamines include N-(2-hydroxyethyl) ethylene diamine, N,N'-bis(2-hydroxyethyl) ethylene diamine, N-(3-hydroxybutyl) tetramethylene diamine, etc.

(2) Heterocyclic-substituted polyamines.

Suitable compounds of this type include hydroxyalkyl-substituted polyamines wherein the polyamines are as described above and the heterocyclic substituent is selected from nitrogen-containing aliphatic and aromatic heterocycles, for example piperazines, imidazolines, pyrimidines, morpholines, etc.

Specific examples of the heterocyclic-substituted polyamines (2) are N-2-aminoethyl piperazine, N-2 and N-3 amino propyl morpholine, N-3(dimethyl amino) propyl piperazine, 2-heptyl-3-(2-aminopropyl) imidazoline, 1,4-bis (2-aminoethyl) piperazine, 1-(2-hydroxy ethyl) piperazine, and 2-heptadecyl-1-(2-hydroxyethyl)-imidazoline, etc.

(3) Aromatic polyamines of the general formula:

wherein Ar is an aromatic nucleus of 6 to 20 carbon atoms, each $R^{15}$ is as defined above and y is from 2 to 8.

Specific examples of the aromatic polyamines (3) are the various isomeric phenylene diamines, the various isomeric naphthalene diamines, etc.

4) The amine reactant may alternatively be a compound of general formula $R^{16}R^{17}NH$ where each of $R^{16}$ and $R^{17}$ independently represents a hydrocarbyl group (as defined herein), preferably a hydrocarbon group (as defined herein), or a hydrogen atom.

Preferably at least one of $R^{16}$ and $R^{17}$ represents a hydrocarbyl group.

Preferably both $R^{16}$ and $R^{17}$ represent a hydrocarbyl group.

Suitable terminal groups of a hydrocarbyl group $R^{16}$ and/or $R^{17}$ may include —$CH_3$, =$CH_2$, —OH, —C(O)OH and derivatives thereof. Suitable derivatives include esters and ethers. Preferably a hydrocarbyl group $R^{16}$ and/or $R^{17}$ does not contain a terminal amine.

A preferred hydrocarbyl group for each of $R^{16}$ and $R^{17}$ is a group of the formula

wherein $R^{18}$ is an alkylene group having from 1 to 10 carbons, preferably from 1 to 5, preferably 1 to 3 carbons, preferably 2 carbons;
wherein $R^{19}$ is an alkylene group having from 1 to 10 carbons, preferably from 1 to 5, preferably 1 to 3 carbons, preferably 2 carbons;
wherein p is an integer from 0 to 10;
wherein X is selected from —$CH_3$, —$CH_2$=$CH_2$, —OH, and —C(O)OH.

A preferred hydrocarbyl group for each of $R^{16}$ and $R^{17}$ is a group of the formula

wherein p is an integer from 0 to 10, preferably 1 to 10, preferably from 1 to 5, preferably from 1 to 3, preferably 1 or 2;
wherein q is an integer from 1 to 10, preferably 1 to 10, preferably from 1 to 5, preferably from 1 to 3, preferably 1 or 2;

wherein r is an integer from 1 to 10, preferably 1 to 10, preferably from 1 to 5, preferably from 1 to 3, preferably 1 or 2; and wherein X is selected from —$CH_3$, —$CH_2$=$CH_2$, —OH, and —C(O)OH.

Preferably X is —$CH_3$, or —OH.

Further amines which may be used to prepare the acylated nitrogen compounds (b) include compounds derived from amines selected from ammonia, alkylamines e.g. butylamine, aminoethylethanolamine, aminopropan-2-ol, 5-aminopentan-1-ol, 2-(2-aminoethoxy)ethanol, monoethanolamine, 3-aminopropan-1-ol, 2-((3-aminopropyl)amino)ethanol, dimethylaminopropylamine, and N-(alkoxyalkyl)-alkanediamines including N-(octyloxyethyl)-1,2-diaminoethane and N-(decyloxypropyl)-N-methyl-1,3-diaminopropane.

Specific examples of amines which may be used in this invention and having a tertiary amino group can include but are not limited to: N,N-dimethyl-aminopropylamine, N,N-diethyl-aminopropylamine, N,N-dimethyl-amino ethylamine. The nitrogen or oxygen containing compounds capable of condensing with the acylating agent and further having a tertiary amino group can further include amino alkyl substituted heterocyclic compounds such as 1-(3-aminopropyl) imidazole and 4-(3-aminopropyl)morpholine, 1-(2-aminoethyl)piperidine, 3,3-diamino-N-methyldi-propylamine, and 3'3-aminobis(N,N-dimethylpropylamine). Other types of compounds capable of condensing with the acylating agent and having a tertiary amino group include alkanolamines including but not limited to triethanolamine, trimethanolamine, N,N-dimethylaminopropanol, N,N-diethylaminopropanol, N,N-diethylaminobutanol, N,N,N-tris(hydroxyethyl)amine and N,N,N-tris(hydroxymethyl)amine.

Many patents have described useful acylated nitrogen compounds including U.S. Pat. Nos. 3,172,892; 3,219,666; 3,272,746; 3,310,492; 3,341,542; 3,444,170; 3,455,831; 3,455,832; 3,576,743; 3,630,904; 3,632,511; 3,804,763, 4,234,435 and 6,821,307.

A preferred acylated nitrogen compound of this class is that made by reacting a poly(isobutene)-substituted succinic acid-derived acylating agent (e.g., anhydride, acid, ester, etc.) wherein the poly(isobutene) substituent has between about 12 to about 200 carbon atoms and the acylating agent has from 1 to 5, preferably from 1 to 3, preferably 1 or 2, succinic-derived acylating groups; with a mixture of ethylene polyamines having 3 to about 9 amino nitrogen atoms, preferably about 3 to about 8 nitrogen atoms, per ethylene polyamine and about 1 to about 8 ethylene groups. These acylated nitrogen compounds are formed by the reaction of a molar ratio of acylating agent:amino compound of from 10:1 to 1:10, preferably from 5:1 to 1:5, more preferably from 2.5:1 to 1:2, more preferably from 2:1 to 1:2 and most preferably from 2:1 to 1:1. In especially preferred embodiments, the acylated nitrogen compounds are formed by the reaction of acylating agent to amino compound in a molar ratio of from 1.8:1 to 1:1.2, preferably from 1.6:1 to 1:1.2, more preferably from 1.4:1 to 1:1.1 and most preferably from 1.2:1 to 1:1. This type of acylated amino compound and the preparation thereof is well known to those skilled in the art and are described in the above-referenced US patents. In other especially preferred embodiments, the acylated nitrogen compounds are formed by the reaction of acylating agent to amino compound in a molar ratio of from 2.5:1 to 1.5:1, preferably from 2.2:1 to 1.8:1.

Another type of acylated nitrogen compound belonging to this class is that made by reacting the afore-described alkylene amines with the afore-described substituted succinic acids or anhydrides and aliphatic mono-carboxylic acids having from 2 to about 22 carbon atoms. In these types of acylated nitrogen compounds, the mole ratio of succinic acid to mono-carboxylic acid ranges from about 1:0.1 to about 1:1. Typical of the monocarboxylic acid are formic acid, acetic acid, dodecanoic acid, butanoic acid, oleic acid, stearic acid, the commercial mixture of stearic acid isomers known as isostearic acid, tolyl acid, etc. Such materials are more fully described in U.S. Pat. Nos. 3,216,936 and 3,250,715.

A further type of acylated nitrogen compound belonging to this class is the product of the reaction of a fatty monocarboxylic acid of about 12-30 carbon atoms and the afore-described alkylene amines, typically, ethylene, propylene or trimethylene polyamines containing 2 to 8 amino groups and mixtures thereof. The fatty mono-carboxylic acids are generally mixtures of straight and branched chain fatty carboxylic acids containing 12-30 carbon atoms. Fatty dicarboxylic acids could also be used. A widely used type of acylated nitrogen compound is made by reacting the afore-described alkylene polyamines with a mixture of fatty acids having from 5 to about 30 mole percent straight chain acid and about 70 to about 95 percent mole branched chain fatty acids. Among the commercially available mixtures are those known widely in the trade as isostearic acid. These mixtures are produced as a by-product from the dimerization of unsaturated fatty acids as described in U.S. Pat. Nos. 2,812,342 and 3,260,671.

The branched chain fatty acids can also include those in which the branch may not be alkyl in nature, for example phenyl and cyclohexyl stearic acid and the chloro-stearic acids. Branched chain fatty carboxylic acid/alkylene polyamine products have been described extensively in the art. See for example, U.S. Pat. Nos. 3,110,673; 3,251,853; 3,326,801; 3,337,459; 3,405,064; 3,429,674; 3,468,639; 3,857,791. These patents are referenced for their disclosure of fatty acid/polyamine condensates for their use in lubricating oil formulations.

Suitably the molar ratio of the acylating group of an acylating agent defined above and the reacting amine group of said amine is in the range 0.5-5:1, preferably 0.8-2.2:1. At a ratio of 1:1 the reaction product is called mono-PIBSI, and at a ratio of 2:1 it is called bis-PIBSI and requires a polyamine as reactant.

Preferred acylated nitrogen compounds for use herein include: the compound formed by reacting a polyisobutylene succinic anhydride (PIBSA) having a PIB molecular weight of 900 to 1100, for example approximately 1000 with aminoethyl ethanolamine or triethylene tetramine; and the compound formed by reacting a PIBSA having a PIB molecular weight of 650 to 850, for example about 750 with tetraethylene pentamine. In each case the ratio of PIBSA to amine is from 1.5:1 to 0.9:1, preferably from 1.2:1 to 1:1. Other preferred acylated nitrogen compounds for use herein include: the compound formed by reacting a polyisobutylene succinic anhydride (PIBSA) having a PIB molecular weight of 900 to 1100, for example approximately 1000 with tetraethylene pentamine, the ratio of PIBSA to amine being from 2.5:1 to 1.5:1, preferably from 2.2:1 to 1.8:1.

c) Hydrocarbyl-Substituted Amines

Hydrocarbyl-substituted amines suitable for use in the present invention are well known to those skilled in the art and are described in a number of patents. Among these are U.S. Pat. Nos. 3,275,554; 3,438,757; 3,454,555; 3,565,804; 3,755,433 and 3,822,209. These patents describe suitable hydrocarbyl amines for use in the present invention including their method of preparation.

d) Mannich Additives

The Mannich additives comprise nitrogen-containing condensates of a phenol, aldehyde and primary or secondary amine Mannich additives can be made by reacting simultaneously or sequentially at least one of each of the following: active hydrogen compound for example a hydrocarbon-substituted phenol (e.g., an alkyl phenol wherein the alkyl group has at least an average of about 8 to 200; preferably at least 12 up to about 200 carbon atoms), having at least one hydrogen atom bonded to an aromatic carbon, with at least one aldehyde or aldehyde-producing material (typically formaldehyde or a precursor thereof) and an amine.

Thus the Mannich additives may be the product of a Mannich reaction between:

(a1) an aldehyde;
(b1) an amine; and
(c1) an optionally substituted phenol.

These compounds may be hereinafter referred to as "the Mannich additives". Thus in some preferred embodiments the present invention provides a gasoline composition comprising a quaternary ammonium salt(s) additive (i) and a Mannich additive.

Any aldehyde may be used as aldehyde component (a1) of the Mannich additive. Preferably the aldehyde component (a1) is an aliphatic aldehyde. Preferably the aldehyde has 1 to 10 carbon atoms, preferably 1 to 6 carbon atoms, more preferably 1 to 3 carbon atoms. Most preferably the aldehyde is formaldehyde.

Amine component (b1) may be at least one amino or polyamino compound having at least one NH group. The amino compounds include primary or secondary monoamines having hydrocarbon substituents of 1 to 30 carbon atoms or hydroxyl-substituted hydrocarbon substituents of 1 to about 30 carbon atoms.

In a preferred embodiment, the amine component (b1) is a polyamine.

Polyamines may be selected from any compound including two or more amine groups. Preferably the polyamine is a (poly)alkylene polyamine (by which is meant an alkylene polyamine or a polyalkylene polyamine; including in each case a diamine, within the meaning of "polyamine"). Preferably the polyamine is a (poly)alkylene polyamine in which the alkylene component has 1 to 6, preferably 1 to 4, most preferably 2 to 3 carbon atoms. Most preferably the polyamine is a (poly) ethylene polyamine (that is, an ethylene polyamine or a polyethylene polyamine).

Preferably the polyamine has 2 to 15 nitrogen atoms, preferably 2 to 10 nitrogen atoms, more preferably 2 to 8 nitrogen atoms.

Preferably the polyamine component (b1) includes the moiety $R^{21}R^{22}NCHR^{23}CHR^{24}NR^{25}R^{26}$ wherein each of $R^{21}$, $R^{22}$, $R^{23}$, $R^{24}$, $R^{25}$ and $R^{26}$ is independently selected from hydrogen, and an optionally substituted alkyl, alkenyl, alkynyl, aryl, alkylaryl or arylalkyl substituent.

Thus the polyamine reactants used to make the Mannich reaction products of the present invention preferably include an optionally substituted ethylene diamine residue.

Preferably at least one of $R^{21}$ and $R^{22}$ is hydrogen. Preferably both of $R^{21}$ and $R^{22}$ are hydrogen.

Preferably at least two of $R^{21}$, $R^{22}$, $R^{25}$ and $R^{26}$ are hydrogen.

Preferably at least one of $R^{23}$ and $R^{24}$ is hydrogen. In some preferred embodiments each of $R^{23}$ and $R^{24}$ is hydrogen. In some embodiments $R^{23}$ is hydrogen and $R^{24}$ is alkyl, for example $C_1$ to $C_4$ alkyl, especially methyl.

Preferably at least one of $R^{25}$ and $R^{26}$ is an optionally substituted alkyl, alkenyl, alkynyl, aryl, alkylaryl or arylalkyl substituent.

In embodiments in which at least one of $R^{21}$, $R^{22}$, $R^{23}$, $R^{24}$, $R^{25}$ and $R^{26}$ is not hydrogen, each is independently selected from an optionally substituted alkyl, alkenyl, alkynyl, aryl, alkylaryl or arylalkyl moiety. Preferably each is independently selected from hydrogen and an optionally substituted C(1-6) alkyl moiety.

In particularly preferred compounds each of $R^{21}$, $R^{22}$, $R^{23}$, $R^{24}$ and $R^{25}$ is hydrogen and $R^{26}$ is an optionally substituted alkyl, alkenyl, alkynyl, aryl, alkylaryl or arylalkyl substituent. Preferably $R^{26}$ is an optionally substituted C(1-6) alkyl moiety.

Such an alkyl moiety may be substituted with one or more groups selected from hydroxyl, amino (especially unsubstituted amino; —NH—, —NH$_2$), sulpho, sulphoxy, C(1-4) alkoxy, nitro, halo (especially chloro or fluoro) and mercapto.

There may be one or more heteroatoms incorporated into the alkyl chain, for example O, N or S, to provide an ether, amine or thioether.

Especially preferred substituents $R^{21}$, $R^{22}$, $R^{23}$, $R^{24}$, $R^{25}$ or $R^{26}$ are hydroxy-C(1-4)alkyl and amino-(C(1-4)alkyl, especially HO—CH$_2$—CH$_2$— and H$_2$N—CH$_2$—CH$_2$—.

Suitably the polyamine includes only amine functionality, or amine and alcohol functionalities.

The polyamine may, for example, be selected from ethylenediamine, diethylenetriamine, triethylenetetramine, tetraethylenepentamine, pentaethylene-hexamine, hexaethyleneheptamine, heptaethyleneoctamine, propane-1,2-diamine, 2(2-amino-ethylamino)ethanol, and N',N'-bis (2-aminoethyl) ethylenediamine (N(CH$_2$CH$_2$NH$_2$)$_3$). Most preferably the polyamine comprises tetraethylenepentamine or ethylenediamine.

Commercially available sources of polyamines typically contain mixtures of isomers and/or oligomers, and products prepared from these commercially available mixtures fall within the scope of the present invention.

The polyamines used to form the Mannich additives of the present invention may be straight chained or branched, and may include cyclic structures.

In preferred embodiments, the Mannich additives of the present invention are of relatively low molecular weight.

Preferably molecules of the Mannich additive product have a number average molecular weight of less than 10000, preferably less than 7500, preferably less than 2000, more preferably less than 1500.

Optionally substituted phenol component (c1) may be substituted with 0 to 4 groups on the aromatic ring (in addition to the phenol OH). For example it may be a tri- or di-substituted phenol. Most preferably component (c1) is a mono-substituted phenol. Substitution may be at the ortho, and/or meta, and/or para position(s).

Each phenol moiety may be ortho, meta or para substituted with the aldehyde/amine residue. Compounds in which the aldehyde residue is ortho or para substituted are most commonly formed. Mixtures of compounds may result. In preferred embodiments the starting phenol is para substituted and thus the ortho substituted product results.

The phenol may be substituted with any common group, for example one or more of an alkyl group, an alkenyl group, an alkyl group, a nitryl group, a carboxylic acid, an ester, an ether, an alkoxy group, a halo group, a further hydroxyl group, a mercapto group, an alkyl mercapto group, an alkyl sulphoxy group, a sulphoxy group, an aryl group, an arylalkyl group, a substituted or unsubstituted amine group or a nitro group.

Preferably the phenol carries one or more optionally substituted alkyl substituents. The alkyl substituent may be optionally substituted with, for example, hydroxyl, halo, (especially chloro and fluoro), alkoxy, alkyl, mercapto, alkyl sulphoxy, aryl or amino residues. Preferably the alkyl group consists essentially of carbon and hydrogen atoms. The substituted phenol may include a alkenyl or alkynyl residue including one or more double and/or triple bonds. Most preferably the component (c1) is an alkyl substituted phenol group in which the alkyl chain is saturated. The alkyl chain may be linear or branched.

Preferably component (c1) is a monoalkyl phenol, especially a para-substituted monoalkyl phenol.

Preferably component (c1) comprises an alkyl substituted phenol in which the phenol carries one or more alkyl chains having a total of less 28 carbon atoms, preferably less than 24 carbon atoms, more preferably less than 20 carbon atoms, preferably less than 18 carbon atoms, preferably less than 16 carbon atoms and most preferably less than 14 carbon atoms.

Preferably the or each alkyl substituent of component (c1) has from 4 to 20 carbons atoms, preferably 6 to 18, more preferably 8 to 16, especially 10 to 14 carbon atoms. In a particularly preferred embodiment, component (c1) is a phenol having a C12 alkyl substituent.

Preferably the or each substituent of phenol component (c1) has a molecular weight of less than 400, preferably less than 350, preferably less than 300, more preferably less than 250 and most preferably less than 200. The or each substituent of phenol component (c) may suitably have a molecular weight of from 100 to 250, for example 150 to 200.

Molecules of component (c1) preferably have a molecular weight on average of less than 1800, preferably less than 800, preferably less than 500, more preferably less than 450, preferably less than 400, preferably less than 350, more preferably less than 325, preferably less than 300 and most preferably less than 275.

Components (a1), (b1) and (c1) may each comprise a mixture of compounds and/or a mixture of isomers.

The Mannich additive is preferably the reaction product obtained by reacting components (a1), (b1) and (c1) in a molar ratio of from 5:1:5 to 0.1:1:0.1, more preferably from 3:1:3 to 0.5:1:0.5.

To form the Mannich additive of the present invention components (a1) and (b1) are preferably reacted in a molar ratio of from 6:1 to 1:4 (aldehyde:polyamine), preferably from 4:1 to 1:2, more preferably from 3:1 to 1:1.

To form a preferred Mannich additive of the present invention the molar ratio of component (a1) to component (c1) (aldehyde:phenol) in the reaction mixture is preferably from 5:1 to 1:4, preferably from 3:1 to 1:2, for example from 1.5:1 to 1:1.1.

Some preferred compounds used in the present invention are typically formed by reacting components (a1), (b1) and (c1) in a molar ratio of 2 parts (a1) to 1 part (b1)±0.2 parts (b1), to 2 parts (c1)±0.4 parts (c1); preferably approximately 2:1:2 (a1:b1:c1).

Some preferred compounds used in the present invention are typically formed by reacting components (a1), (b1) and (c1) in a molar ratio of 2 parts (a1) to 1 part (b1)±0.2 parts (b1), to 1.5 parts (c1)±0.3 parts (c1); preferably approximately 2:1:1.5 (a1:b1:c1).

Suitable treat rates of the quaternary ammonium salt(s) additive (i) and when present the Mannich additive will depend on the desired performance and on the type of engine in which they are used. For example different levels of additive may be needed to achieve different levels of performance.

e) Aromatic Esters of a Polyalkylphenoxyalkanol

The aromatic ester component which may be employed additive composition is an aromatic ester of a polyalkylphenoxyalkanol and has the following general formula:

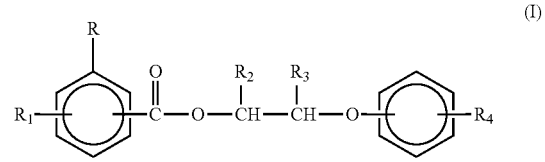

or a fuel-soluble salt(s) thereof wherein R is hydroxy, nitro or —(CH2)x-NR$_5$R$_6$, wherein R$_5$ and R$_6$ are independently hydrogen or lower alkyl having 1 to 6 carbon atoms and x is 0 or 1;

R$_1$ is hydrogen, hydroxy, nitro or —NR$_7$R$_5$ wherein R$_7$ and R$_5$ are independently hydrogen or lower alkyl having 1 to 6 carbon atoms;

R$_2$ and R$_3$ are independently hydrogen or lower alkyl having 1 to 6 carbon atoms; and R$_4$ is a polyalkyl group having an average molecular weight in the range of about 450 to 5,000.

The preferred aromatic ester compounds employed in the present invention are those wherein R is nitro, amino, N-alkylamino, or —CH$_2$NH$_2$ (aminomethyl). More preferably, R is a nitro, amino or —CH$_2$NH$_2$ group. Most preferably, R is an amino or —CH$_2$NH$_2$ group, especially amino. Preferably, R$_1$ is hydrogen, hydroxy, nitro or amino. More preferably, R$_1$ is hydrogen or hydroxy. Most preferably, R$_1$ is hydrogen. Preferably, R$_4$ is a polyalkyl group having an average molecular weight in the range of about 500 to 3,000, more preferably about 700 to 3,000, and most preferably about 900 to 2,500. Preferably, the compound has a combination of preferred substituents.

Preferably, one of R$_2$ and R$_3$ is hydrogen or lower alkyl of 1 to 4 carbon atoms, and the other is hydrogen. More preferably, one of R$_2$ and R$_3$ is hydrogen, methyl or ethyl, and the other is hydrogen. Most preferably, R$_2$ is hydrogen, methyl or ethyl, and R$_3$ is hydrogen.

When R and/or R$_1$ is an N-alkylamino group, the alkyl group of the N-alkylamino moiety preferably contains 1 to 4 carbon atoms. More preferably, the N-alkylamino is N-methylamino or N-ethylamino.

Similarly, when R and/or R$_1$ is an N,N-dialkylamino group, each alkyl group of the N,N-dialkylamino moiety preferably contains 1 to 4 carbon atoms. More preferably, each alkyl group is either methyl or ethyl. For example, particularly preferred N,N-dialkylamino groups are N,N-dimethylamino, N-ethyl-N-methylamino and N,N-diethylamino groups.

A further preferred group of compounds are those wherein R is amino, nitro, or —CH$_2$NH$_2$ and R$_1$ is hydrogen or hydroxy. A particularly preferred group of compounds are those wherein R is amino, R$_1$, R$_2$ and R$_3$ are hydrogen, and R$_4$ is a polyalkyl group derived from polyisobutene.

It is preferred that the R substituent is located at the meta or, more preferably, the para position of the benzoic acid moiety, i.e. para or meta relative to the carbonyloxy group. When R$_1$ is a substituent other than hydrogen, it is particularly preferred that this R$_1$ group be in a meta or para position relative to the carbonyloxy group and in an ortho position relative to the R substituent. Further, in general, when $R_1$ is other than hydrogen, it is preferred that one of R or $R_1$ is located para to the carbonyloxy group and the other is located meta to the carbonyloxy group. Similarly, it is preferred that the $R_4$ substituent on the other phenyl ring is located para or meta, more preferably para, relative to the ether linking group.

The aromatic esters (e) will generally have a molecular weight in the range from about 700 to about 3,500, preferably from about 700 to about 2,500.

Fuel-soluble salt(s)s of the compounds (e) can be readily prepared for those compounds containing an amino or substituted amino group and such salt(s)s are contemplated to be useful for preventing or controlling engine deposits. Suitable salt(s)s include, for example, those obtained by protonating the amino moiety with a strong organic acid, such as an alkyl- or arylsulfonic acid. Preferred salt(s)s are derived from toluenesulfonic acid and methanesulfonic acid.

When the R or $R_1$ substituent is a hydroxy group, suitable salt(s)s can be obtained by deprotonation of the hydroxy group with a base. Such salt(s)s include salt(s)s of alkali metals, alkaline earth metals, ammonium and substituted ammonium salt(s)s. Preferred salt(s)s of hydroxy-substituted compounds include alkali metal, alkaline earth metal and substituted ammonium salt(s)s.

f) Quaternary Ammonium Salt

The quaternary ammonium salt additive is suitably the reaction product of a nitrogen-containing species having at least one tertiary amine group and a quaternising agent.

The nitrogen containing species may be selected from:
(x) the reaction product of a hydrocarbyl-substituted acylating agent and a compound comprising at least one tertiary amine group and a primary amine, secondary amine or alcohol group;
(y) a Mannich reaction product comprising a tertiary amine group; and
(z) a polyalkylene substituted amine having at least one tertiary amine group.

Examples of quaternary ammonium salt and methods for preparing the same are described in the following patents, which are hereby incorporated by reference, US2008/0307698, US2008/0052985, US2008/0113890 and US2013/031827.

The preparation of some suitable quaternary ammonium salt additives in which the nitrogen-containing species includes component (x) is described in WO 2006/135881 and WO2011/095819.

Component (y) is a Mannich reaction product having a tertiary amine. The preparation of quaternary ammonium salts formed from nitrogen-containing species including component (y) is described in US 2008/0052985.

The preparation of quaternary ammonium salt additives in which the nitrogen-containing species includes component (z) is described for example in US 2008/0113890.

To form the quaternary ammonium salt additive (f) the nitrogen-containing species having a tertiary amine group is reacted with a quaternising agent.

The quaternising agent may suitably be selected from esters and non-esters.

Preferred quaternising agents for use herein include dimethyl oxalate, methyl 2-nitrobenzoate, methyl salicylate and styrene oxide or propylene oxide optionally in combination with an additional acid.

An especially preferred additional quaternary ammonium salt for use herein is formed by reacting methyl salicylate or dimethyl oxalate with the reaction product of a polyisobutylene-substituted succinic anhydride having a PIB number average molecular weight of 700 to 1300 and dimethylaminopropylamine.

Other suitable quaternary ammonium salts include quaternised terpolymers, for example as described in US2011/0258917; quaternised copolymers, for example as described in US2011/0315107; and the acid-free quaternised nitrogen compounds disclosed in US2012/0010112.

Further suitable quaternary ammonium compounds for use in the present invention include the quaternary ammonium compounds described in the applicants copending applications WO2011095819, WO2013/017889, WO2015/011506, WO2015/011507, WO2016/016641 and PCT/GB2016/052312.

The fuel compositions of the invention may contain, in addition to the quaternary ammonium salt additive(s) (i) and the gasoline, and the other components (ii) (selected from (a)-(f) described above) when present, unreacted raw materials and other reaction products and any of the other additives conventionally added to gasoline as, for example, other detergents, dispersants, anti-oxidants, anti-icing agents, metal deactivators, lubricity additives, friction modifiers, dehazers, corrosion inhibitors, dyes, markers, octane improvers, anti-valve-seat recession additives, stabilisers, demulsifiers, antifoams, odour masks, conductivity improvers, combustion improvers, etc."

Such further ingredients could in principle be added separately to quaternary ammonium additives(s) (i) but it is preferred for reasons of convenience and consistency of dosing to add them with quaternary ammonium salt additive (s) (i) and—when present, with further additive components (ii)—in a common additive composition.

Preferably the additives(s) (i) and (ii) (when present) is/are present in the fuel in the fuel storage tank which supplies the engine. Although they could be mixed into the fuel in the storage tank, preferably they are present in bulk fuel which is pumped into the storage tank.

The present invention relates to improving the performance of spark ignition engines by combusting gasoline fuel compositions comprising a quaternary ammonium salt additive.

The quaternary ammonium salt additives may be added to gasoline fuel at any convenient place in the supply chain. For example, the additives may be added to fuel at the refinery, at a distribution terminal or after the fuel has left the distribution terminal. If the additive is added to the fuel after it has left the distribution terminal, this is termed an aftermarket application. Aftermarket applications include such circumstances as adding the additive to the fuel in the delivery tanker, directly to a customer's bulk storage tank, or directly to the end user's vehicle tank. Aftermarket applications may include supplying the fuel additive in small bottles suitable for direct addition to fuel storage tanks or vehicle tanks.

Controlling deposits in the specification is intended to cover one or more of: reducing existing deposits ("clean-up"); reducing deposit formation ("keep-clean"); modifying deposits so as to reduce their negative effects.

It has surprisingly been found that the gasoline compositions used in this invention achieve good control of deposits in spark ignition gasoline engines.

It has surprisingly been found that the gasoline compositions used in this invention achieve good control of deposits even in the demanding context of the direct injection spark ignition gasoline engine.

This control of deposits may lead to a significant reduction in maintenance costs and/or an increase in power and/or an improvement in fuel economy.

The second aspect of the present invention provides a method of controlling deposits in spark ignition engine. Preferably the engine is a direct injection spark ignition gasoline engine.

Suitably the present invention provides a method of controlling deposits in a direct injection spark ignition gasoline engine, the method comprising the method comprising adding into the gasoline to be combusted:
(i) one or more quaternary ammonium salt additives of the first aspect and
(ii) optionally, one or more additional components selected from a)-f) described above.

Suitably the present invention provides a method of improving the efficiency of a direct injection spark ignition gasoline engine, the method comprising adding into the gasoline to be combusted:
(i) one or more quaternary ammonium salt additives of the first aspect; and
(ii) optionally, one or more additional components selected from a)-f) described above.

Suitably the present invention provides a method of operating a direct injection spark ignition gasoline engine, the method comprising adding into the gasoline to be combusted:
(i) one or more quaternary ammonium salt additives of the first aspect; and
(ii) optionally, one or more additional components selected from a)-f) described above wherein the method provides one or more of:—
  improved fuel economy
  reduced maintenance
  less frequent overhaul or replacement of injectors
  improved driveability
  improved power
  improved acceleration Suitably the present invention provides the use of (i) one or more quaternary ammonium salt additives as defined in the first aspect and, optionally of (ii) one or more additional components selected from a)-f) described above; added into gasoline to control deposits in a direct injection spark ignition gasoline engine.

Suitably the present invention provides the use of (i) one or more quaternary ammonium salt additives as defined in the first aspect and, optionally of (ii) one or more additional components selected from a)-f) described above; added into gasoline to improve efficiency in a direct injection spark ignition gasoline engine.

Suitably the present invention provides the use of a gasoline comprising (i) one or more quaternary ammonium salt additives as defined in the first aspect and, optionally of (ii) one or more additional components selected from a)-f) described above; in a direct injection spark ignition gasoline engine to provide one or more of:—
  improved fuel economy
  reduced maintenance
  less frequent overhaul or replacement of injectors
  improved driveability
  improved power
  improved acceleration Any feature of the invention may be combined with any other feature as appropriate.

The invention will now be further described with reference to the following non-limiting examples. In the examples which follow the values given in parts per million (ppm) for treat rates denote active agent amount, not the amount of a formulation as added, and containing an active agent. All parts per million are by weight.

EXAMPLE 1

Additive A1, an additive of the invention was prepared as follows:

A mixture of alkenes having 20 to 24 carbon atoms was heated with 1.2 molar equivalents of maleic anhydride. On completion of the reaction excess maleic anhydride was removed by distillation. The anhydride value of the substituted succinic anhydride product was measured as 2.591 $mmolg^{-1}$.

This product was then heated with one molar equivalent of polypropylene glycol having a number average molecular weight of 425, and the reaction was monitored by FTIR.

The resultant material was reacted with one molar equivalent dimethyl aminopropanol at 140° C. in xylene and the reaction monitored until constant acid valve and FTIR spectra were obtained. Volatiles were then removed in vacuo to afford a mixed diester.

This mixed diester product was reacted with 1.5 molar equivalents of butylene oxide, 6 molar equivalents of water and one molar equivalents of acetic acid at 60° C. in toluene for 6 hours. Volatiles were removed in vacuo to provide the quaternary ammonium salt A1.

Additive A2 was prepared using a method analogous to that used to prepare additive A1 except that tripropylene glycol was used in place of polypropylene glycol.

Additive A3 was prepared using a method analogous to that used to prepare additive A1 except that polyethylene glycol having a number average molecular weight of 400 was used in place of the polypropylene glycol.

Additive A4 was prepared using a method analogue to that used to prepare additive A1 except that in the last step the diester was reacted with one molar equivalent of dimethyl oxalate in place of the butylene oxide/acetic acid.

Additive A5 was prepared using a method analogous to the preparation of additive A2 except in the last step the diester was reacted with one molar equivalent of dimethyl oxalate in place of the butylene oxide/acetic acid.

Additive A6 was prepared using a method analogous to that used in the preparation of additive A3 except in the last step the diester was reacted with one molar equivalent of dimethyl oxalate in place of the butylene oxide/acetic acid.

Additive A7 was prepared using a method analogous to that used to prepare additive A1 except that in the last step 1 molar equivalent of methyl salicylate was used as the quaternising agent.

Additive A8 was prepared using a method analogous to the preparation of additive A2 except that in the last step 1 molar equivalents of methyl salicylate was used as the quaternising agent.

Additive A9 was prepared using a method analogous to that used in the preparation of additive A3 except that in the last step 1 molar equivalents of methyl salicylate was used as the quaternising agent.

The reagents used in the preparation of additives A1 to A9 are summarised in the table below and further additives prepared from polyisobutenyl substituted succinic acid derivatives and other amines, alcohols and quaternising agents are also listed in table 1. Compounds A10 to A15 were prepared by methods analogous to those described in relation to compounds A1 to A9.

TABLE 1

| Example No | Succinic anhydride substituent | Alcohol | Amine | Quaternising agent |
|---|---|---|---|---|
| A1 | C20-24 | Poly(propylene glycol) Mn425 | N,N-dimethylamino propanol | Butylene oxide + acetic acid |
| A2 | C20-24 | Poly(propylene glycol) Mn425 | N,N-dimethylamino propanol | Butylene oxide + acetic acid |
| A3 | C20-24 | Poly(ethylene glycol) Mn400 | N,N-dimethylamino propanol | Butylene oxide + acetic acid |
| A4 | C20-24 | Poly(propylene glycol) Mn425 | N,N-dimethylamino propanol | Dimethyl oxalate |
| A5 | C20-24 | tri(propylene glycol) | N,N-dimethylamino propanol | Dimethyl oxalate |
| A6 | C20-24 | Poly(ethylene glycol) Mn400 | N,N-dimethylamino propanol | Dimethyl oxalate |
| A7 | C20-24 | Poly(propylene glycol) Mn425 | N,N-dimethylamino propanol | Methyl Salicylate |
| A8 | C20-24 | tri(propylene glycol) | N,N-dimethylamino propanol | Methyl Salicylate |
| A9 | C20-24 | Poly(ethylene glycol) Mn400 | N,N-dimethylamino propanol | Methyl Salicylate |
| A10 | 1000PIB | Poly(ethlylene glycol) 600 | N,N-dimethylamino propylamine | Methyl Salicylate |
| A11 | 1000PIB | Tridecanol.(PO)$_{15}$ | N,N-dimethylamino propanol | 1,2 epoxydodecane + acetic acid |
| A12 | 1000PIB | Poly(propylene glycol) Mn425 | N,N-dimethylamino propanol | Butylene oxide + acetic acid |
| A13 | 1000PIB | Tridecanol.(PO)$_{15}$ | N,N-dimethylamino propanol | Styrene oxide + acetic acid |
| A14 | 550PIB | tri(propylene glycol) | N,N-dimethylamino propanol | Methyl Salicylate |
| A15 | 1000PIB | tri(propylene glycol) | N,N-dimethylamino propanol | Methyl Salicylate |

"Tridecanol.(PO)$_{15}$" is the reaction product of a $C_{13}$ alkanol and an average of 15 moles of propylene oxide per molecule.

EXAMPLE 2

Additive A15 was dosed into a gasoline base fuel and tested according to the following procedure:

The GDI test procedure uses an engine that has been proposed as a CEC industry standard test engine.

The test engine is the VW EA111 1,4 L TSI (CAVE) engine with 132 kW, representing the Skoda version of the EA111 engine family The test procedure is performed with new 6-hole injectors, type 03C906036E/F. The injector run-in procedure is performed at high load for 4 hours.

The test procedure is a steady state test at an engine speed of 2000 rpm and a constant torque of 56 Nm (=5 bar mean effective pressure).

The engine is run on a base fuel (ULG95) for a 48 hour 'dirty up phase' and then a 24 hour 'clean up phase' using the base fuel+105 mg/kg of additive.

Nozzle coking is measured as change of injection timing. Due to nozzle coking, the hole diameter of the injector holes is reduced and the injection time adjusted by the Engine Control Unit (ECU) accordingly. The injection time in milliseconds is a direct readout from the ECU via ECU control software.

The results of the test are shown in FIG. 1.

The invention claimed is:

1. A gasoline fuel or lubricating composition comprising a quaternary ammonium salt of formula (I):

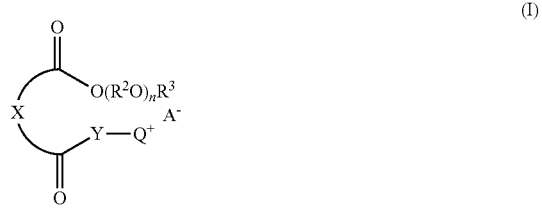

wherein X is a linking group; Y is O, NH or NR$^1$ wherein R$^1$ is H or an optionally substituted hydrocarbyl group; Q$^+$ is a moiety that includes a quaternary ammonium cation; A⁻ is an anion; R² is an optionally substituted alkylene group; R³ is hydrogen or an optionally substituted hydrocarbyl group; and n is 0 or a positive integer; provided that n is not 0 when R³ is hydrogen.

2. A method of improving the performance of an engine, the method comprising combusting in the engine a gasoline fuel composition comprising as an additive a quaternary ammonium salt of formula (I):

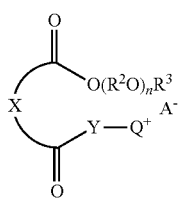
(I)

wherein X is a linking group; Y is O, NH or NR¹ wherein R¹ is H or an optionally substituted hydrocarbyl group; Q⁺ is a moiety that includes a quaternary ammonium cation; A⁻ is an anion; R² is an optionally substituted alkylene group; R³ is hydrogen or an optionally substituted hydrocarbyl group; and n is 0 or a positive integer; provided n is not 0 when R³ is hydrogen.

3. The composition according to claim 1 wherein the quaternary ammonium salt additive is prepared by reacting:
 (a) a hydrocarbyl substituted dicarboxylic acid or anhydride thereof; with
 (b) an alcohol of formula $R^3(OR^2)_nOH$;
 (c) a reactive alcohol or amine including a tertiary amino group; and
 (d) a quaternising agent.

4. The composition according to claim 1 wherein X is an optionally substituted alkylene or arylene group and R⁴ is an optionally substituted hydrocarbyl group.

5. The composition according to claim 1 wherein n is 0 and R³ is an optionally substituted alkyl or alkenyl group having 4 to 40 carbon atoms.

6. The composition according to claim 1 wherein each R² is ethylene or propylene.

7. The composition according to claim 6 wherein R³ is hydrogen and n is at least 1.

8. The composition according to claim 6 wherein R³ is an optionally substituted alkyl group having 4 to 40 carbon atoms and n is from 1 to 40.

9. The composition according to claim 1 wherein Q⁺ is a group having the formula:

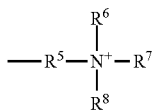

wherein R⁵ is an optionally substituted alkylene, arylene or alkenylene group and each of R⁶, R⁷ and R⁸ is independently an optionally substituted hydrocarbyl group.

10. The composition according to claim 9 wherein R⁵ is an optionally substituted alkylene group having 1 to 6 carbon atoms, R⁶ is $C_1$ to $C_6$ alkyl, R⁷ is $C_1$ to $C_6$ alkyl and R⁸ is an unsubstituted $C_1$ to $C_6$ alkyl group or a hydroxy substituted $C_1$ to $C_{40}$ alkyl group.

11. The composition according to claim 1 wherein A⁻ is a carboxylate anion.

12. The composition according to claim 1 wherein the quaternary ammonium salt additive is prepared by reacting:
 (a) an optionally substituted succinic acid or anhydride thereof;
 (b) an alcohol of formula $H(OR^2)_nOH$ or $R^3OH$;
 (c) a reactive alcohol including a tertiary amino group; and
 (d) a quaternising agent.

13. The composition according to claim 1 wherein the quaternary ammonium salt additive is prepared by reacting:
 (a) a succinic acid or anhydride thereof substituted with a $C_{20}$ to $C_{24}$ alkyl or alkenyl group;
 (b) a polypropylene glycol or butanol;
 (c) dimethylaminopropanol; and
 a quaternising agent selected from the group consisting of: methyl salicylate, dimethyl oxalate and a hydrocarbyl epoxide in combination with an acid.

14. The composition according to claim 1 wherein the composition is a lubricating composition.

15. The composition according to claim 1 wherein the composition is a gasoline fuel composition.

16. The composition according to claim 15 wherein the gasoline fuel composition comprises one or more further detergents selected from the group consisting of:
 a) carrier oils
 b) acylated nitrogen compounds which are the reaction product of a carboxylic acid-derived acylating agent and an amine
 c) hydrocarbyl-substituted amines wherein the hydrocarbyl substituent is substantially aliphatic and contains at least 8 carbon atoms
 d) mannich base additives comprising nitrogen-containing condensates of a phenol, aldehyde and primary or secondary amine
 e) aromatic esters of a polyalkylphenoxyalkanol; and
 f) quaternary ammonium salts.

17. The composition according to claim 15 wherein the gasoline fuel composition comprises a mixture of two or more quaternary ammonium salt additives.

18. The method according to claim 2 wherein the engine is a direct injection spark ignition engine.

19. The method according to claim 2 which achieves "keep clean" performance.

20. The method according to claim 2 which achieves "clean up" performance.

21. The method according to claim 2 which combats injector deposits.

22. The method according to claim 21 wherein the deposits are internal injector deposits.

23. The method according to claim 2 which achieves an improvement in performance of one or more of:
 improved fuel economy
 reduced maintenance
 less frequent overhaul or replacement of injectors
 improved driveability
 improved power; or
 improved acceleration.

* * * * *